United States Patent
Tsuyuki

(10) Patent No.: US 11,341,638 B2
(45) Date of Patent: May 24, 2022

(54) MEDICAL IMAGE DIAGNOSTIC SYSTEM AND METHOD FOR GENERATING TRAINED MODEL

(71) Applicant: CANON MEDICAL SYSTEMS CORPORATION, Otawara (JP)

(72) Inventor: Masaharu Tsuyuki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 70 days.

(21) Appl. No.: 16/727,144

(22) Filed: Dec. 26, 2019

(65) Prior Publication Data

US 2020/0219252 A1 Jul. 9, 2020

(30) Foreign Application Priority Data

Dec. 26, 2018 (JP) .............................. JP2018-242893

(51) Int. Cl.
*G06T 7/00* (2017.01)
*A61B 6/00* (2006.01)
*A61B 6/03* (2006.01)
*G06N 20/00* (2019.01)

(52) U.S. Cl.
CPC ............ *G06T 7/0012* (2013.01); *A61B 6/032* (2013.01); *A61B 6/481* (2013.01); *A61B 6/488* (2013.01); *G06N 20/00* (2019.01); *G06T 2207/10081* (2013.01); *G06T 2207/20081* (2013.01); *G06T 2207/20084* (2013.01); *G06T 2207/20182* (2013.01); *G06T 2207/30004* (2013.01)

(58) Field of Classification Search
CPC ......... G06T 7/0012; G06T 2207/10081; G06T 2207/20081; G06T 2207/20084; G06T 2207/20182; G06T 2207/30004; G06N 20/00; A61B 6/032; A61B 6/481; A61B 6/488
See application file for complete search history.

(56) References Cited

U.S. PATENT DOCUMENTS

| 10,383,590 B2 * | 8/2019 | Vaz ........................... A61B 6/54 |
| 2014/0107479 A1 | 4/2014 | Klaiman et al. |
| 2015/0310638 A1 * | 10/2015 | Jia ........................... A61B 6/541 382/131 |

(Continued)

*Primary Examiner* — Vu Le
*Assistant Examiner* — Julius Chai
(74) *Attorney, Agent, or Firm* — Oblon, McClelland, Maier & Neustadt, L.L.P.

(57) ABSTRACT

A medical image diagnostic system includes processing circuitry configured (to): (a) acquire a trained model generated by using, as learning data, images or signals corresponding to a first group of time-series images acquired by performing a first pre-scan on a first patient injected with a contrast agent in a first examination, as well as timing information about timing of a transition from a first pre-scan to a first main scan in a first examination, and information about appropriateness of the timing; and (b) determine appropriate timing of a transition from a second pre-scan to a second main scan by inputting, to the trained model, images or signals corresponding to a second group of time-series images acquired by performing the second pre-scan on a second patient injected with a contrast agent in the second examination different from the first examination.

19 Claims, 14 Drawing Sheets

(56) References Cited

U.S. PATENT DOCUMENTS

| | | | |
|---|---|---|---|
| 2016/0073997 A1* | 3/2016 | Yoda | A61B 6/54 |
| | | | 378/16 |
| 2017/0293009 A1 | 10/2017 | Meade et al. | |
| 2018/0071452 A1* | 3/2018 | Sharma | G16H 30/40 |
| 2018/0182133 A1 | 6/2018 | Tanaka | |
| 2019/0167213 A1* | 6/2019 | Jain | G06T 11/005 |
| 2019/0231288 A1* | 8/2019 | Profio | A61B 6/0407 |
| 2020/0163639 A1* | 5/2020 | De Man | A61B 6/54 |

* cited by examiner

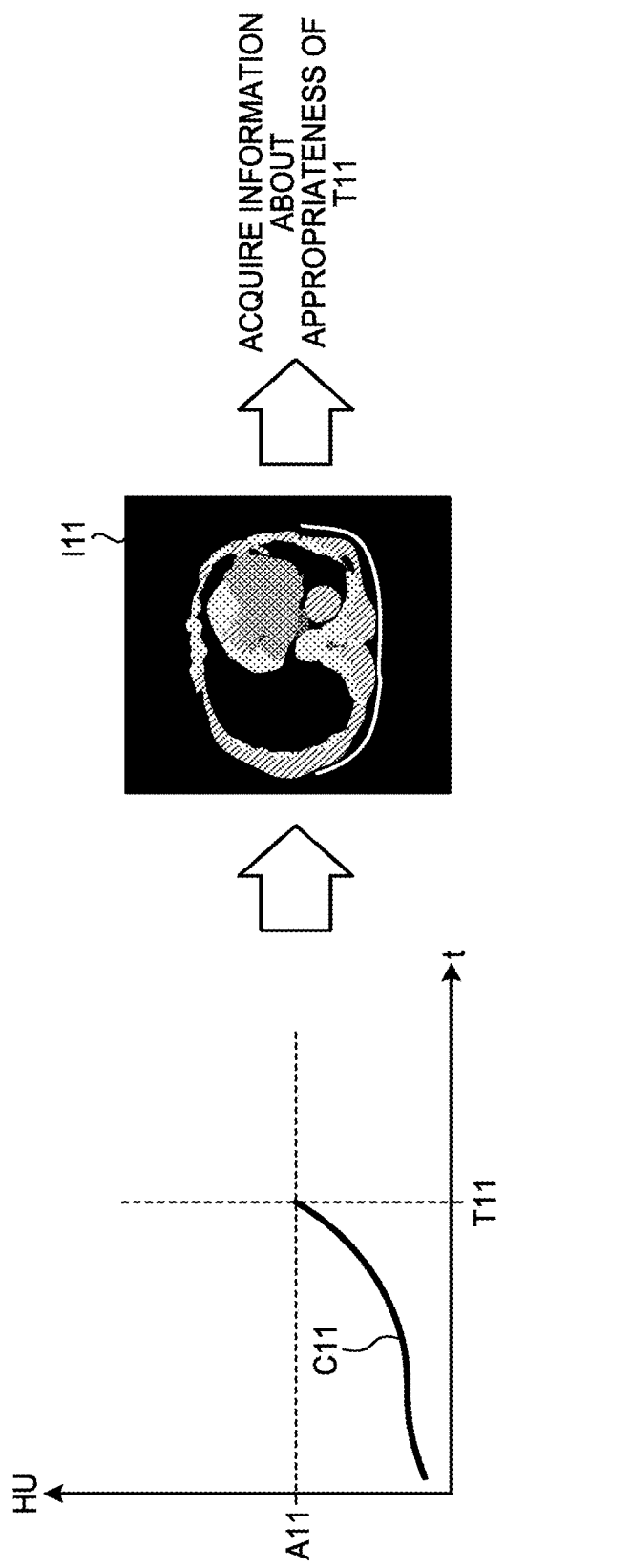

FIG.4B

| INPUT-SIDE LEARNING DATA | OUTPUT-SIDE LEARNING DATA |
|---|---|
| TDCC11, TIME T11 | APPROPRIATE |
| TDCC12, TIME T12 | LATE |
| TDCC13, TIME T13 | EARLY |
| ⋮ | ⋮ |

FIG.6B

| INPUT-SIDE LEARNING DATA | OUTPUT-SIDE LEARNING DATA |
|---|---|
| TDCC15, TIME T15 | LATE |
| TDCC151, TIME T151 | APPROPRIATE |
| TDCC152, TIME T152 | EARLY |
| ⋮ | ⋮ |

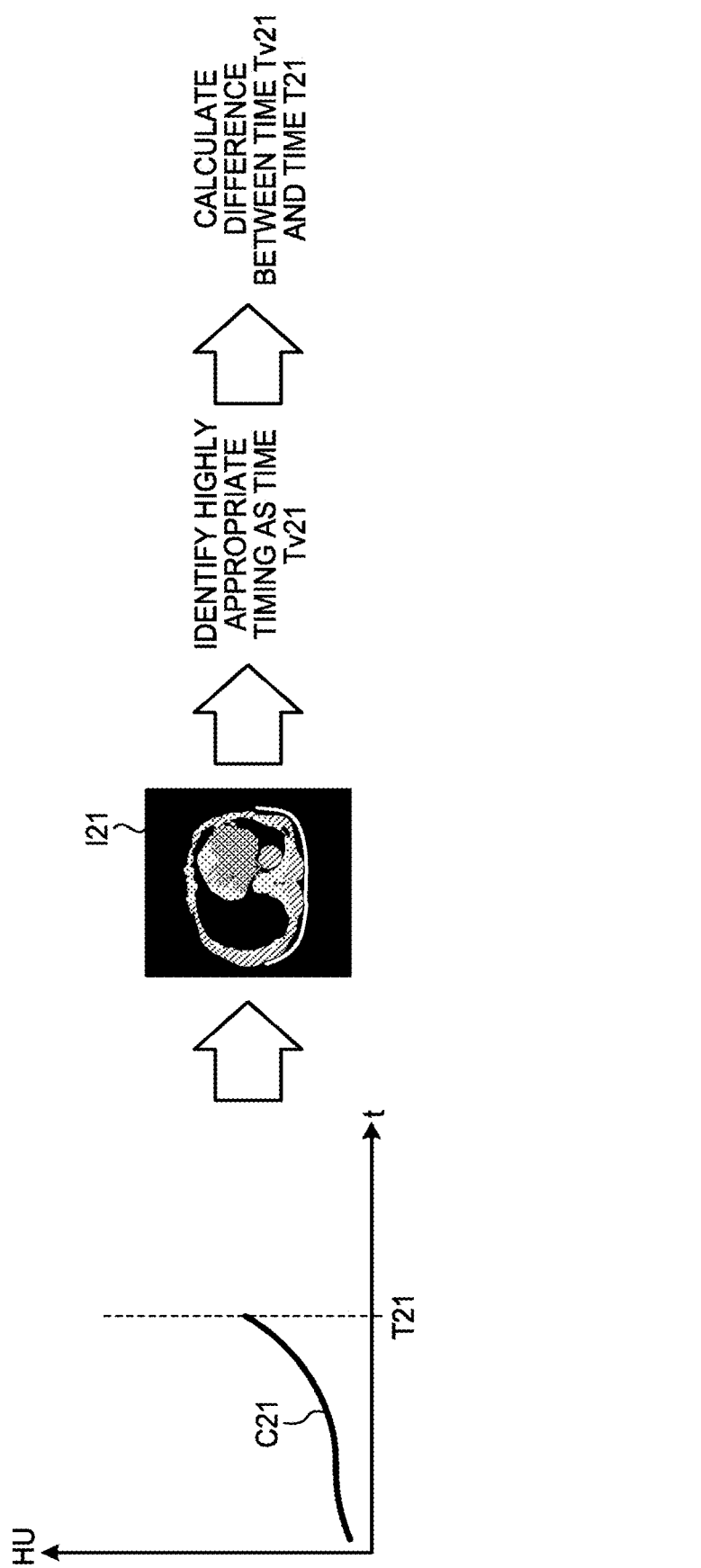

FIG.9B

| INPUT-SIDE DATA | OUTPUT-SIDE DATA |
|---|---|
| TDCC21, TIME T21 | +1.5 SECONDS |
| TDCC22, TIME T22 | 0 SECONDS |
| TDCC23, TIME T23 | -1 SECOND |
| ⋮ | ⋮ |

MEDICAL IMAGE DIAGNOSTIC SYSTEM AND METHOD FOR GENERATING TRAINED MODEL

CROSS-REFERENCE TO RELATED APPLICATIONS

This application is based upon and claims the benefit of priority from Japanese Patent Application No. 2018-242893, filed on Dec. 26, 2018; the entire contents of which are incorporated herein by reference.

FIELD

Embodiments described herein relate generally to a medical image diagnostic system and a method for generating a trained model.

BACKGROUND

For medical examinations (hereinafter, "examinations") using an X-ray Computed Tomography (CT) apparatus, a technique is known by which a pre-scan is performed prior to a main scan so as to determine the timing of the main scan by using a group of time-series images acquired in the pre-scan. In one example, after a contrast agent is injected in an examined subject, signal intensities in a Region Of Interest (ROI) are sequentially acquired on the basis of the pre-scan, so that a transition is made to the main scan at a time when any of the signal intensities exceeds a threshold value. However, because it is difficult to set an optimal threshold value, it is not easy to appropriately determine the timing of the main scan.

BRIEF DESCRIPTION OF THE DRAWINGS

FIG. 4A is a drawing illustrating an example of timing of a transition from a pre-scan to a main scan according to the first embodiment;

FIG. 4B is a table illustrating examples of learning data used for generating a trained model according to the first embodiment;

FIG. 6B is a drawing illustrating examples of the learning data used for generating the trained model according to the first embodiment;

FIG. 9A is a drawing illustrating an example of a learning data acquiring process according to a second embodiment;

FIG. 9B is a drawing illustrating examples of learning data used for generating a trained model according to the second embodiment;

DETAILED DESCRIPTION

A medical image diagnostic system includes processing circuitry. The processing circuitry is configured to acquire a trained model generated by using, as learning data, at least one selected from among a first group of time-series images acquired by performing a first pre-scan on a first patient injected with a contrast agent in a first examination using the medical image diagnostic system, a first group of time-series partial images being generated on the basis of the first group of time-series images and corresponding to a first region of interest of the first patient, and first time-series information about signal intensities in the first region of interest generated on the basis of the first group of time-series images, as well as timing information about timing of a transition from the first pre-scan to a first main scan in the first examination, and information about appropriateness of the timing. The processing circuitry is configured to determine, in a second examination different from the first examination, appropriate timing of a transition from a second pre-scan to a second main scan by inputting, to the trained model, at least one selected from among a second group of time-series images acquired by performing the second pre-scan on a second patient injected with a contrast agent in the second examination different from the first examination, a second group of time-series partial images being generated on the basis of the second group of time-series images and corresponding to a second region of interest of the second patient, and second time-series information about signal intensities in the second region of interest generated on the basis of the second group of time-series images.

In the following sections, exemplary embodiments of a medical image diagnostic system and a method for generating a trained model will be explained, with reference to the accompanying drawings.

To begin with, a first embodiment will be explained. In the first embodiment, an X-ray diagnostic system 1 including an X-ray CT apparatus 10, an image storage apparatus 20, and a medical information processing apparatus 30 will be explained.

Figure 1:
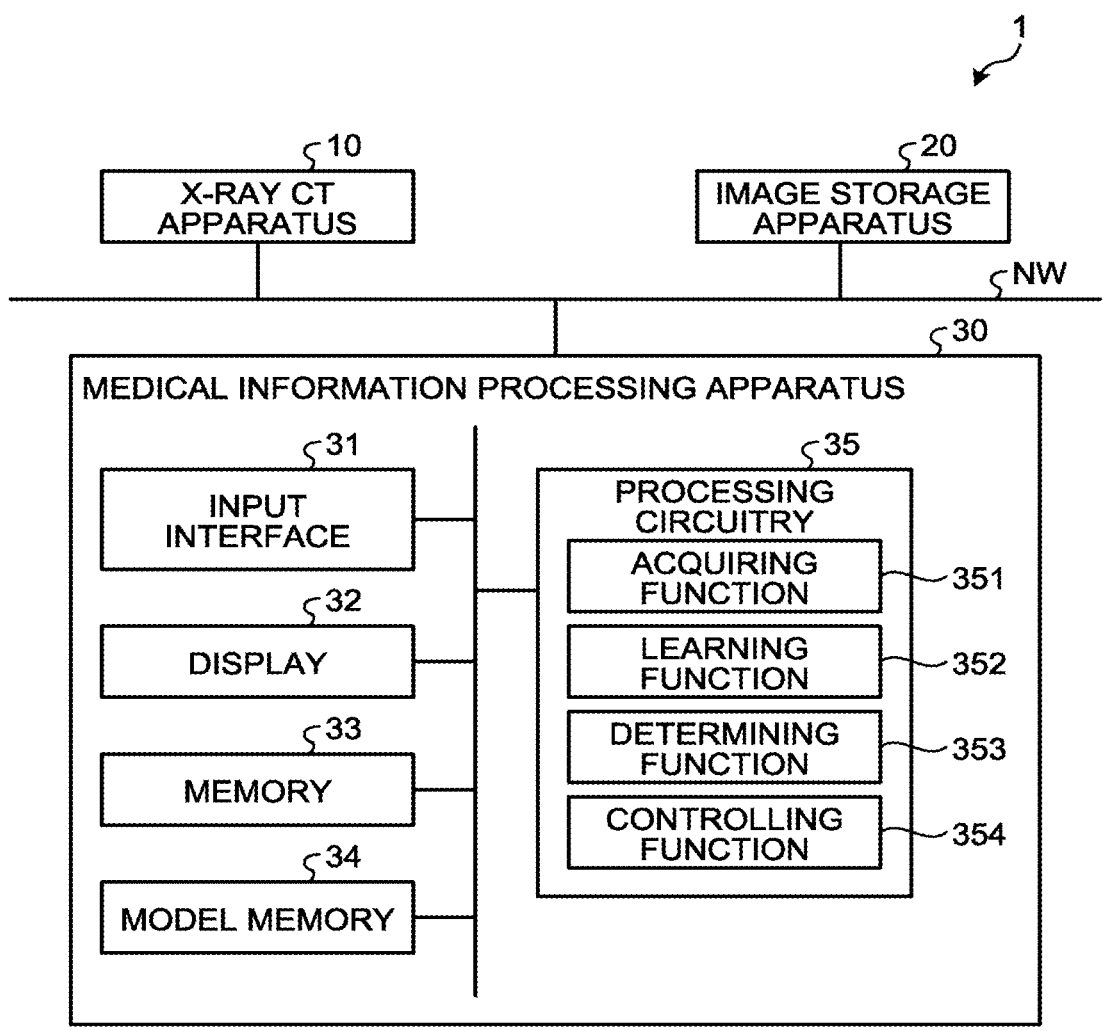
FIG. 1 is a block diagram illustrating an exemplary configuration of an X-ray diagnostic system according to a first embodiment.

FIG. 1 is a block diagram illustrating an exemplary configuration of the X-ray diagnostic system 1 according to the first embodiment. As illustrated in FIG. 1, the X-ray diagnostic system 1 according to the first embodiment includes the X-ray CT apparatus 10, the image storage apparatus 20, and the medical information processing apparatus 30. As illustrated in FIG. 1, the X-ray CT apparatus 10, the image storage apparatus 20, and the medical information processing apparatus 30 are connected to one another via a network NW.

The X-ray CT apparatus 10 is an apparatus configured to acquire image data from an examined subject (hereinafter, "patient"). For example, the X-ray CT apparatus 10 acquires a group of time-series image data by performing a pre-scan on the patient. Further, the X-ray CT apparatus 10 transmits the acquired group of time-series image data to the medical information processing apparatus 30. Further, for example, the X-ray CT apparatus 10 is configured to transition from the pre-scan to a main scan with timing determined by the medical information processing apparatus 30 and to acquire CT image data. Further, the X-ray CT apparatus 10 is configured to transmit the acquired CT image data to the image storage apparatus 20. A configuration of the X-ray CT apparatus 10 will be explained later.

The image storage apparatus 20 is an apparatus configured to store various types of image data acquired by apparatuses included in the X-ray diagnostic system 1. For example, the image storage apparatus 20 receives the CT image data acquired by the X-ray CT apparatus 10 and store the CT image data into a memory provided on the inside or outside thereof. For example, the image storage apparatus 20 is realized by using a computer device such as a server apparatus.

The medical information processing apparatus 30 is configured to acquire, via the network NW, the group of time-series image data acquired in the pre-scan and to determine the timing of the main scan performed by the X-ray CT apparatus 10 on the basis of the acquired group of image data. For example, the medical information processing apparatus 30 is configured to generate a trained model used for determining appropriate timing of the transition from the pre-scan to the main scan, by using learning data acquired in a first examination. Further, by using the generated trained model, the medical information processing apparatus 30 is configured to determine timing of a transition from a pre-scan to a main scan in a second examination. Processes performed by the medical information processing apparatus 30 will be explained later. For example, the medical information processing apparatus 30 is realized by using a computer device such as a workstation.

As long as the connection via the network NW is possible, the locations in which the X-ray CT apparatus 10, the image storage apparatus 20, and the medical information processing apparatus 30 are installed are arbitrary. For example, the medical information processing apparatus 30 may be installed in a hospital different from the hospital in which the X-ray CT apparatus 10 is installed. In other words, the network NW may be structured with a local network closed within a hospital or may be a network mediated by the Internet. Further, although FIG. 1 illustrates the single X-ray CT apparatus 10, the X-ray diagnostic system 1 may include two or more X-ray CT apparatuses 10.

As illustrated in FIG. 1, the medical information processing apparatus 30 includes an input interface 31, a display 32, a memory 33, a model memory 34, and processing circuitry 35.

The input interface 31 is configured to receive various types of input operations from an operator, to convert the received input operations into electrical signals, and to output the electrical signals to the processing circuitry 35. For example, the input interface 31 is realized by using a mouse, a keyboard, a trackball, a switch, a button, a joystick, a touchpad on which input operations can be performed by touching the operation surface thereof, a touch screen in which a display screen and a touchpad are integrally formed, contactless input circuitry using an optical sensor, audio input circuitry, and/or the like. The input interface 31 may be configured by using a tablet terminal or the like capable of wirelessly communicating with the main body of the medical information processing apparatus 30. Further, the input interface 31 does not necessarily have to include one or more physical operation component parts such as a mouse and a keyboard. For instance, possible examples of the input interface 31 include electrical signal processing circuitry configured to receive an electrical signal corresponding to an input operation from an external input device provided separately from the medical information processing apparatus 30 and to output the electrical signal to the processing circuitry 35.

The display 32 is configured to display various types of information. For example, the display 32 is configured to display a Graphical User Interface (GUI) used for receiving various types of instructions and various types of settings from the operator via the input interface 31. Further, the display 32 is configured to display various types of images acquired with respect to patients. For example, the display 32 is configured to display the group of time-series images acquired in the pre-scan. For example, the display 32 may be a liquid crystal display device or a Cathode Ray Tube (CRT) display device. The display 32 may be of a desktop type or may be configured with a tablet terminal or the like capable of wirelessly communicating with the main body of the medical information processing apparatus 30.

The memory 33 is realized, for example, by using a semiconductor memory element such as a Random Access Memory (RAM) or a flash memory, or a hard disk, an optical disk, or the like. For example, the memory 33 has stored therein computer programs (hereinafter "programs") used by the circuitry included in the medical information processing apparatus 30 to realize the functions thereof. The memory 33 may be realized by using a group of servers (a cloud) connected to the medical information processing apparatus 30 via the network NW.

The model memory 34 is realized, for example, by using a semiconductor memory element such as a RAM or a flash memory, or a hard disk, an optical disk, or the like. In this situation, the model memory 34 is an example of a storage unit. For example, the model memory 34 is configured to store therein the trained model used for determining appropriate timing of the transition from the pre-scan to the main scan. The trained model stored in the model memory 34 will be explained later. The model memory 34 may be realized by using a cloud.

The processing circuitry 35 is configured to control operations of the entirety of the medical information processing apparatus 30, by executing an acquiring function 351, a learning function 352, a determining function 353, and a controlling function 354. In this situation, the acquiring function 351 is an example of the acquiring unit. The learning function 352 is an example of a learning unit. The determining function 353 is an example of the determining unit.

For example, by reading and executing a program corresponding to the acquiring function 351 from the memory 33, the processing circuitry 35 acquires, from the X-ray CT apparatus 10, the group of time-series image data acquired by performing the pre-scan on the patient injected with the contrast agent in the first examination using the X-ray diagnostic system 1. Further, on the basis of the acquired group of time-series image data, the acquiring function 351 is configured to acquire time-series information about signal intensities in a region of interest of the patient. Processes performed by the acquiring function 351 will be explained later.

Further, for example, by reading and executing a program corresponding to the learning function 352 from the memory 33, the processing circuitry 35 generates the trained model. In one example, the learning function 352 is configured to generate the trained model used for determining appropriate timing of the transition from a pre-scan to a main scan in the second examination different from the first examination, by using the time-series information acquired by the acquiring function 351 and timing information about the timing of the transition from the pre-scan to the main scan in the first examination as input-side learning data and using information about appropriateness of the timing of the transition from the pre-scan to the main scan in the first examination as output-side learning data. Processes performed by the learning function 352 will be explained later.

Further, for example, by reading and executing a program corresponding to the determining function 353 from the memory 33, the processing circuitry 35 determines the appropriate timing of the transition from the pre-scan to the main scan in the second examination, by using the trained model generated by the learning function 352. In one example, the determining function 353 is configured to acquire, from the X-ray CT apparatus 10, the group of time-series image data acquired by performing the pre-scan on the patient injected with the contrast agent in the second examination. Subsequently, on the basis of the acquired group of time-series image data, the determining function 353 is configured to acquire the time-series information about the signal intensities in the region of interest of the patient. Further, by inputting the acquired time-series information to the trained model, the determining function 353 is configured to determine the appropriate timing of the transition from the pre-scan to the main scan in the second examination. Processes performed by the determining function 353 will be explained later.

Further, for example, by reading and executing a program corresponding to the controlling function 354 from the memory 33, the processing circuitry 35 controls displays on the display 32. For example, the controlling function 354 is configured to cause the display 32 to display the group of time-series image data acquired in the pre-scan. Further, the controlling function 354 is configured to transmit various types of data via the network NW. In one example, the controlling function 354 is configured to transmit the appropriate timing of the transition from the pre-scan to the main scan in the second examination that was determined by the determining function 353, to the X-ray CT apparatus. Processes performed by the controlling function 354 will be explained later.

In the medical information processing apparatus 30 illustrated in FIG. 1, the processing functions are stored in the memory 33 in the form of computer-executable programs. The processing circuitry 35 is a processor configured to realize the functions corresponding to the programs by reading and executing the programs from the memory 33. In other words, the processing circuitry 35 that has read the programs has the functions corresponding to the read programs.

With reference to FIG. 1, the example was explained in which the single processing circuit (i.e., the processing circuitry 35) realizes the acquiring function 351, the learning function 352, the determining function 353, and the controlling function 354; however, it is also acceptable to structure the processing circuitry 35 by combining together a plurality of independent processors, so that the functions are realized as a result of the processors executing the programs. Further, it is also acceptable to realize the processing functions of the processing circuitry 35 so as to be distributed among, or integrated together in, one or more processing circuits as appropriate.

Figure 2:
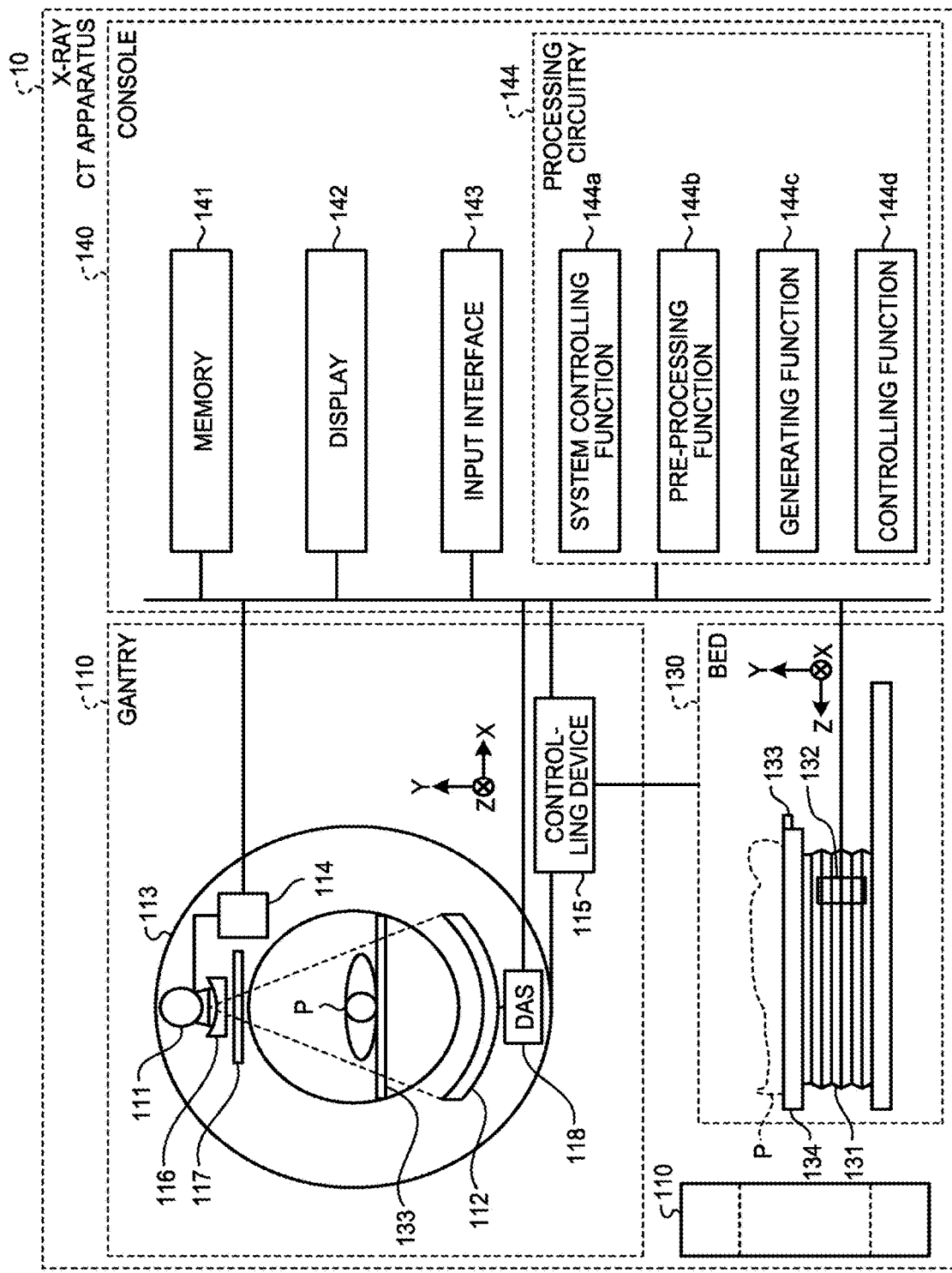
FIG. 2 is a block diagram illustrating an exemplary configuration of an X-ray CT apparatus according to the first embodiment.

Next, the X-ray CT apparatus 10 will be explained with reference to FIG. 2. FIG. 2 is a block diagram illustrating an exemplary configuration of the X-ray CT apparatus 10 according to the first embodiment. As illustrated in FIG. 2, the X-ray CT apparatus 10 includes a gantry 110, a bed 130, and a console 140.

In FIG. 2, the rotation axis of a rotating frame 113 in a non-tilted state or the longitudinal direction of a tabletop 133 of the bed 130 corresponds to a Z-axis direction. Further, an axial direction orthogonal to the Z-axis direction and parallel to the floor surface will be referred to as an X-axis direction. Further, an axial direction orthogonal to the Z-axis direction and perpendicular to the floor surface will be referred to as a Y-axis direction. FIG. 2 illustrates the gantry 110 from multiple directions for explanation purposes and illustrates the example in which the X-ray CT apparatus 10 includes the one gantry 110.

The gantry 110 includes an X-ray tube 111, an X-ray detector 112, the rotating frame 113, an X-ray high voltage device 114, a controlling device 115, a wedge 116, a collimator 117, and a Data Acquisition System (DAS) 118.

The X-ray tube 111 is a vacuum tube including a negative pole (a filament) configured to generate thermo electrons and a positive pole (a target) configured to generate X-rays in response to collisions of the thermo electrons. With high voltage applied thereto from the X-ray high-voltage device 114, the X-ray tube 111 is configured to generate the X-rays to be radiated onto a patient P, by emitting the thermo electrons from the negative pole toward the positive pole.

The X-ray detector 112 includes a plurality of detecting elements configured to detect X-rays. The detecting elements in the X-ray detector 112 are configured to detect X-rays that were radiated from the X-ray tube 111 and have passed through the patient P and to output a signal corresponding to a detected X-ray amount to the DAS 118. The X-ray detector 112 includes, for example, a plurality of rows of detecting elements in each of which a plurality of detecting elements are arranged in a channel direction along an arc centered on a focal point of the X-ray tube 111. For example, the X-ray detector 112 has a structure in which the plurality of rows in each of which the plurality of detecting elements are arranged in the channel direction are arranged in the row direction (a slice direction).

For example, the X-ray detector 112 is a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of X-rays that have become incident thereto. The grid is disposed on the surface of the scintillator array positioned on the X-ray incident side and includes an X-ray blocking plate that absorbs scattered X-rays. The grid may be referred to as a collimator (a one-dimensional collimator or a two-dimensional collimator). The optical sensor array has a function of converting outputs from the scintillators into electric signals corresponding to the amounts of light and may include, for example, optical sensors such as photodiodes. Alternatively, the X-ray detector 112 may be a detector of a direct conversion type including semiconductor elements configured to convert incident X-rays into electric signals.

The rotating frame 113 is an annular frame configured to support the X-ray tube 111 and the X-ray detector 112 so as to oppose each other and configured to rotate the X-ray tube 111 and the X-ray detector 112 via the controlling device 115. For example, the rotating frame 113 is cast by using aluminum. In addition to supporting the X-ray tube 111 and the X-ray detector 112, the rotating frame 113 is also capable of further supporting the X-ray high-voltage device 114, the wedge 116, the collimator 117, the DAS 118, and the like. Also, the rotating frame 113 is capable of further supporting various types of structures that are not illustrated in FIG. 2. In the gantry 110, the rotating frame 113 and the part that rotates and moves together with the rotating frame 113 may hereinafter be referred to as a rotating part.

The X-ray high-voltage device 114 includes: a high-voltage generating device including electric circuitry such as a transformer, a rectifier, and the like and configured to generate the high voltage to be applied to the X-ray tube 111; and an X-ray controlling device configured to control the output voltage in accordance with the X-rays generated by the X-ray tube 111. The high-voltage generating device may be of a transformer type or of an inverter type. Further, the X-ray high-voltage device 114 may be provided for the rotating frame 113 or for a fixed frame (not illustrated).

The controlling device 115 includes: processing circuitry having a Central Processing Unit (CPU) or the like; and a driving mechanism configured with a motor, an actuator, and the like. The controlling device 115 is configured to receive an input signal from an input interface 143 and to control operations of the gantry 110 and the bed 130. For example, the controlling device 115 exercises control over the rotating of the rotating frame 113, the tilting of the gantry 110, operations of the bed 130 and the tabletop 133, and the like. The controlling device 115 may be provided for the gantry 110 or for the console 140.

The wedge 116 is a filter used for adjusting the amount of X-rays radiated from the X-ray tube 111. More specifically, the wedge 116 is a filter configured to pass and attenuate the X-rays radiated from the X-ray tube 111, so that the X-rays radiated from the X-ray tube 111 onto the patient P have a predetermined distribution. For example, the wedge 116 may be a wedge filter or a bow-tie filter and is a filter acquired by processing aluminum or the like so as to have a predetermined target angle and a predetermined thickness.

The collimator 117 is structured with lead plates or the like used for narrowing down the radiation range of the X-rays that have passed through the wedge 116 and is configured to form a slit with a combination of the plurality of lead plates or the like. The collimator 117 may be referred to as an X-ray limiter. Further, although FIG. 2 illustrates the example in which the wedge 116 is arranged between the X-ray tube 111 and the collimator 117, the collimator 117 may be arranged between the X-ray tube 111 and the wedge 116. In that situation, the wedge 116 is configured to pass and attenuate the X-rays that were radiated from the X-ray tube 111 and of which the radiation range has been limited by the collimator 117.

The DAS 118 is configured to acquire the signals of the X-rays detected by the detecting elements included in the X-ray detector 112. For example, the DAS 118 includes an amplifier configured to perform an amplifying process on the electric signals output from the detecting elements; and an Analog/Digital (A/D) converter configured to convert the electric signals into digital signals. The DAS 118 is configured to generate detection data. The DAS 118 may be realized by using a processor, for example.

The data generated by the DAS 118 is transmitted, via optical communication, from a transmitter provided for the rotating frame 113 and including a Light Emitting Diode (LED) to a receiver provided in a non-rotating part (e.g., a fixed frame, which is not illustrated in FIG. 2) of the gantry 110 and including a photodiode and is further transferred to the console 140. In this situation, the non-rotating part may be, for example, the fixed frame or the like configured to rotatably support the rotating frame 113. The method for transmitting the data from the rotating frame 113 to the non-rotating part of the gantry 110 does not necessarily have to be optical communication and may be any contactless data transfer method or any contact-type data transfer method.

The bed 130 is a device configured to have the patient P placed thereon and to move the patient P who is to be scanned. The bed 130 includes a base 131, a bed driving device 132, the tabletop 133, and a supporting frame 134. The base 131 is a casing configured to support the supporting frame 134 so as to be movable in the vertical direction. The bed driving device 132 is a driving mechanism configured to move the tabletop 133 on which the patient P is placed, along the longitudinal direction of the tabletop 133 and includes a motor, an actuator, and the like. The tabletop 133 provided on the top face of the supporting frame 134 is a board on which the patient P is placed. In addition to moving the tabletop 133, the bed driving device 132 may also be configured to move the supporting frame 134 along the longitudinal direction of the tabletop 133.

The console 140 includes a memory 141, a display 142, an input interface 143, and processing circuitry 144. Although the console 140 is described as being separate from the gantry 110, the gantry 110 may include either the console 140 or one or more constituent elements of the console 140.

The memory 141 is realized by using, for example, a semiconductor memory element such as a RAM or a flash memory, or a hard disk, an optical disk, or the like. For example, the memory 141 is configured to store therein projection data and image data reconstructed on the basis of projection data. Further, for example, the memory 141 is configured to store therein one or more programs used by the circuits included in the X-ray CT apparatus 10 for realizing the functions thereof. Alternatively, the memory 141 may be realized with a cloud.

The display 142 is configured to display various types of information. For example, the display 142 is configured to display various types of images generated by the processing circuitry 144 and to display a GUI or the like used for receiving various types of operations from an operator. For example, the display 142 may be a liquid crystal display device or a CRT display device. The display 142 may be of a desktop type or may be configured with a tablet terminal or the like capable of wirelessly communicating with the main body of the console 140.

The input interface 143 is configured to receive various types of input operations from the operator, to convert the received input operations into electric signals, and to output the electric signals to the processing circuitry 144. For example, the input interface 143 is realized by using a mouse, a keyboard, a trackball, a switch, a button, a joystick, a touchpad on which an input operation can be performed by touching the operation surface thereof, a touch screen in which a display screen and a touchpad are integrally formed, contactless input circuitry using an optical sensor, audio input circuitry, and/or the like. The input interface 143 may be provided for the gantry 110. Alternatively, the input interface 143 may be configured by using a tablet terminal or the like capable of wirelessly communicating with the main body of the console 140. Further, the input interface 143 does not necessarily have to include one or more physical operation component parts such as a mouse and a keyboard. For instance, possible examples of the input interface 143 include electric signal processing circuitry configured to receive an electric signal corresponding to an input operation from an external input device provided separately from the console 140 and to output the electric signal to the processing circuitry 144.

The processing circuitry 144 is configured to control operations of the entirety of the X-ray CT apparatus 10 by executing a system controlling function 144a, a pre-processing function 144b, a generating function 144c, and a controlling function 144d.

For example, by reading and executing a program corresponding to the system controlling function 144a from the memory 141, the processing circuitry 144 performs a scan on the patient P. For example, by controlling the X-ray high voltage device 114, the system controlling function 144a is configured to supply the high voltage to the X-ray tube 111. Accordingly, the X-ray tube 111 is configured to generate the X-rays to be radiated onto the patient P. Further, by controlling the bed driving device 132, the system controlling function 144a is configured to move the patient P to the inside of the image taking opening of the gantry 110. Further, the system controlling function 144a is configured to adjust the opening degree and the position of the collimator 117. Further, by controlling the controlling device 115, the system controlling function 144a is configured to rotate the rotating part. While a scan is performed by the system controlling function 144a, the DAS 118 is configured to acquire the signals of the X-rays from the detecting elements of the X-ray detector 112 and to generate the detection data.

Further, by reading and executing a program corresponding to the pre-processing function 144b from the memory 141, the processing circuitry 144 performs pre-processing processes on the detection data output from the DAS 118. For example, the pre-processing function 144b is configured to perform pre-processing processes such as a logarithmic converting process, an offset correcting process, a sensitivity correcting process among the channels, a beam hardening correction, and/or the like, on the detection data output from the DAS 118. The data resulting from the pre-processing processes may be referred to as raw data. The detection data before the pre-processing processes and the raw data resulting from the pre-processing processes may collectively be referred to as projection data.

By reading and executing a program corresponding to the generating function 144c from the memory 141, the processing circuitry 144 generates image data on the basis of the raw data resulting from the corrections. For example, the generating function 144c is configured to generate the image data by performing a reconstructing process while using a filtered back projection method, a successive approximation method, or the like on the raw data resulting from the corrections. In one example, the generating function 144c is configured to generate a group of time-series image data on the basis of a plurality of pieces of raw data in a time series acquired in the pre-scan. In one example, the generating function 144c is configured to generate CT image data on the basis of raw data acquired in the main scan.

Further, for example, by reading and executing a program corresponding to the controlling function 144d from the memory 141, the processing circuitry 144 controls the display on the display 142. For example, on the basis of input operations received from the operator via the input interface 143 or the like, the controlling function 144d is configured to convert the CT image data generated by the generating function 144c into a display-purpose CT image (e.g., tomographic data on an arbitrary cross-sectional plane or three-dimensional image data) by using a publicly-known method. Further, the controlling function 144d is configured to cause the display 142 to display the display-purpose CT image resulting from the conversion. Further, via the network NW, the controlling function 144d is configured to transmit various types of data. In one example, the controlling function 144d is configured to transmit the group of time-series image data acquired in the pre-scan to the medical information processing apparatus 30.

In the X-ray CT apparatus 10 illustrated in FIG. 2, the processing functions are stored in the memory 141 in the form of computer-executable programs. The processing circuitry 144 is a processor configured to realize the functions corresponding to the programs by reading and executing the programs from the memory 141. In other words, the processing circuitry 144 that has read the programs has the functions corresponding to the read programs.

With reference to FIG. 2, the example was explained in which the single processing circuit (i.e., the processing circuitry 144) realizes the system controlling function 144a, the pre-processing function 144b, the generating function 144c, and the controlling function 144d; however, it is also acceptable to structure the processing circuitry 144 by combining together a plurality of independent processors, so that the functions are realized as a result of the processors executing the programs. Further, it is also acceptable to realize the processing functions of the processing circuitry 144 so as to be distributed among, or integrated together in, one or more processing circuits as appropriate.

The term "processor" used in the above explanations denotes, for example, a CPU, a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 33 or the memory 141.

FIGS. 1 and 2 illustrate the examples in which the single storage circuit (the memory 33 or 141) stores therein the programs corresponding to the processing functions. However, possible embodiments are not limited to these examples. For instance, it is acceptable to provide a plurality of storage circuits in a distributed manner, so that the processing circuitry 35 reads a corresponding program from each of the individual storage circuits. Similarly, it is also acceptable to provide a plurality of storage circuits in a distributed manner, so that the processing circuitry 144 reads a corresponding program from each of the individual storage circuits. Further, instead of saving the programs in either the memory 33 or the memory 141, it is also acceptable to directly incorporate the programs into the circuits of one or more processors. In that situation, the one or more processors realize the functions by reading and executing the programs incorporated in the circuits thereof.

Further, the processing circuitry 35 and the processing circuitry 144 may realize the functions by using a processor of an external device connected via the network NW. For example, the processing circuitry 35 may realize the functions illustrated in FIG. 1, by reading and executing the programs corresponding to the functions from the memory 33, while using a group of servers (a cloud) connected to the medical information processing apparatus 30 via the network NW as computational resources.

The X-ray diagnostic system 1 including the X-ray CT apparatus 10, the image storage apparatus 20, and the medical information processing apparatus 30 has thus been explained. The X-ray diagnostic system 1 structured as described above is configured to appropriately determine the timing of the main scan, with processes performed by the processing circuitry 35.

To begin with, an example will be explained in which the timing of the main scan is determined by using a threshold value. For example, in an examination E11 performed on a patient P11, the X-ray CT apparatus 10 performs a pre-scan on the patient P11 injected with a contrast agent, prior to the main scan. The patient P11 is an example of the patient P illustrated in FIG. 2. In this situation, the X-ray CT apparatus 10 sequentially transmits image data acquired in the pre-scan to the medical information processing apparatus 30. Further, the acquiring function 351 included in the medical information processing apparatus 30 sequentially acquires the transmitted image data. In other words, the acquiring function 351 acquires a group of time-series image data.

Figure 3:
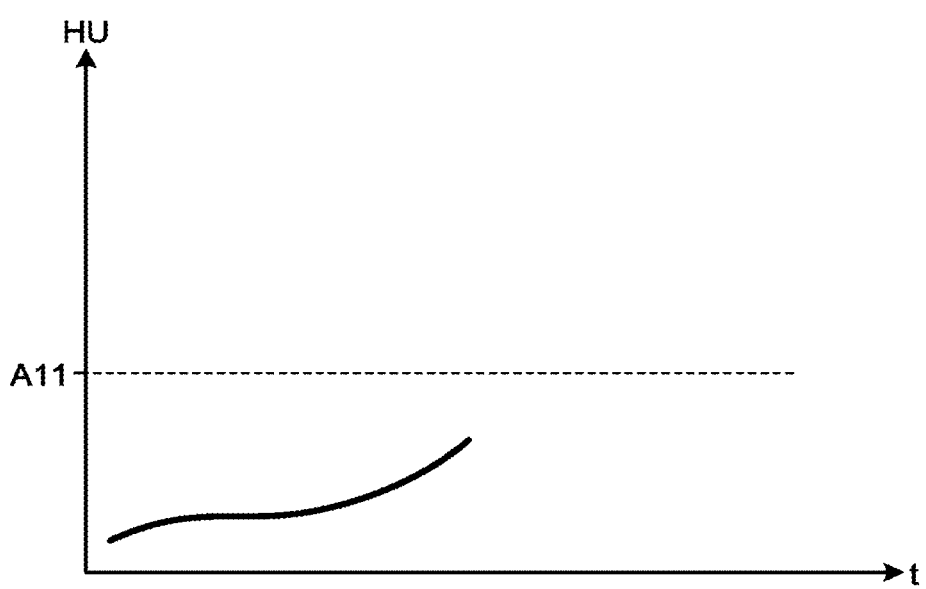
FIG. 3 is a chart illustrating an example of a Time Density Curve (TDC) according to the first embodiment.

Further, on the basis of the acquired group of time-series image data, the acquiring function 351 acquires a Time Density Curve (TDC) illustrated in FIG. 3. In this situation, the TDC is an example of time-series information about signal intensities in a region of interest of the patient P11. In other words, on the basis of the group of time-series image data acquired from the X-ray CT apparatus 10, the acquiring function 351 acquires the times-series information about the signal intensities in the region of interest of the patient P11. FIG. 3 is a chart illustrating an example of the TDC according to the first embodiment.

More specifically, at first, the system controlling function 144a sets a target site of the main scan and a target site of the pre-scan. In this situation, the target site of the main scan is, for example, a site to be treated in the examination E11. Further, the target site of the pre-scan is, for example, a site to be monitored for the purpose of measuring the timing with which the target site of the main scan is to be contrast-enhanced.

In one example, when the target site of the main scan is the "heart", the system controlling function 144a sets the "aorta" as a target site of the pre-scan. In this situation, when a contrast agent is injected into a vein of the patient P11, the contrast agent goes through the left atrium and the left ventricle of the patient P11 and reaches the aorta. Accordingly, by monitoring the "aorta" in the pre-scan and performing the main scan in accordance with the reaching status of the contrast agent to the "aorta", it is possible to acquire CT image data in which the left atrium and the left ventricle of the patient P11 are clearly contrast-enhanced. The target site of the pre-scan may manually be set by the operator or may automatically be set by the system controlling function 144a in accordance with the target site of the main scan.

After that, the system controlling function 144a performs the pre-scan on the "aorta" of the patient P11 injected with the contrast agent. Further, while the pre-scan is performed by the system controlling function 144a, the DAS 118 acquires the signals of the X-rays from the detecting elements included in the X-ray detector 112 and sequentially generates projection data. Further, the pre-processing function 144b sequentially performs the pre-processing processes on the projection data output from the DAS 118. Further, every time the pre-processing function 144b performs the pre-processing process on the projection data, the generating function 144c sequentially generates image data on the basis of the projection data on which the pre-processing process has been performed. In other words, the generating function 144c sequentially generates slices rendering the target site "aorta" of the pre-scan. Further, the controlling function 144d sequentially transmits the generated image data to the medical information processing apparatus 30. Also, the acquiring function 351 sequentially acquires the transmitted image data.

Further, the acquiring function 351 sets a region of interest of the patient P11. For example, the acquiring function 351 sets, as the region of interest, a region including the "aorta" of the patient P11 in the image data acquired from the X-ray CT apparatus 10. In one example, the controlling function 354 causes the display 32 to display the acquired image data. Further, by receiving an operation to set the region of interest from the operator who referenced the image data, the acquiring function 351 sets the region of interest. Alternatively, the acquiring function 351 may automatically set the region of interest by performing an image processing process.

After that, the acquiring function 351 acquires the TDC on the basis of the signal intensities in the region of interest in the group of time-series image data acquired in the pre-scan. For example, the acquiring function 351 acquires the TDC illustrated in FIG. 3, by plotting Hounsfield Unit (HU) values (pixel values) in the region of interest in correspondence with a time axis, with respect to pieces of image data in the group of time-series image data. In FIG. 3, the horizontal axis expresses time t, whereas the vertical axis expresses the HU values in the region of interest.

Further, every time image data is newly acquired from the X-ray CT apparatus 10, the acquiring function 351 sequentially updates the TDC, by plotting the HU values in the region of interest in the newly-acquired image data in correspondence with the time axis. In the following sections, the TDC updated up to the time T11 in FIG. 4A will be referred to as a TDC C11. As indicated by the TDC C11 in FIG. 4A, when the HU value has reached a threshold value A11 at the time T11, the determining function 353 determines the time T11 as the timing of the transition from the pre-scan to the main scan in the examination E11. FIG. 4A is a drawing illustrating the example of the timing of the transition from the pre-scan to the main scan according to the first embodiment.

Further, the controlling function 354 transmits the determined time T11 to the X-ray CT apparatus 10. The X-ray CT apparatus 10 transitions from the pre-scan to the main scan at the time T11 and acquires CT image data Il1 illustrated in FIG. 4A. In other words, by being triggered by the HU value in the region of interest reaching the threshold value, the X-ray CT apparatus 10 transitions from the pre-scan to the main scan and acquires the CT image data Il1. As a result of the transition to the main scan, the pre-scan ends, and the updating of the TDC also ends.

In this situation, when the threshold value A11 is optimal, it means that optimal CT image data Il1 is acquired of the "heart" of the patient P11 in the main scan. However, it is not easy to optimize the threshold value A11, because there are individual differences in the diffusion speed of the contrast agent and the magnitudes of the HU values in the region of interest. In other words, the time T11 of the transition from the pre-scan to the main scan in the examination E11 is not necessarily appropriate and may be later or earlier than appropriate timing in some situations.

After that, the learning function 352 acquires information about appropriateness of the time T11 of the transition from the pre-scan to the main scan in the examination E11. For example, as illustrated in FIG. 4A, the learning function 352 acquires the information about appropriateness of the time T11, by using the CT image data Il1 acquired in the main scan.

In this situation, as one example, a situation will be explained in which the operator plans to observe the left ventricle of the patient P11 in the examination E11. In that situation, when the left atrium appearing in the CT image data Ill is rendered more clearly than the left ventricle is, there is a possibility that, if the transition had been made from the pre-scan to the main scan with timing later than the time T11, the contrast agent in a higher density distributed in the left atrium at the time T11 might have flowed into the left ventricle, so that CT image data rendering the left ventricle more clearly could have been acquired. Accordingly, when the left atrium appearing in the CT image data Ill is rendered more clearly than the left ventricle is, the learning function 352 is able to determine that the time T11 is "early".

Further, as another example, when the CT image data Ill hardly renders the left atrium, it is considered that the ejection of the contrast agent from the heart of the patient P11 has substantially been completed by the time Ill. In other words, even though the left ventricle appears in the CT image data Ill, there is a possibility that, if the transition had been made from the pre-scan to the main scan with timing earlier than the time T11, CT image data rendering the left ventricle more clearly could have been acquired. Accordingly, when the CT image data Ill hardly renders the left atrium, the learning function 352 is able to determine that the time T11 is "late".

Further, as yet another example, when the left ventricle is rendered more clearly in the CT image data Ill than the left atrium and the aorta are, the learning function 352 is able to determine that the time T11 is "appropriate". In other words, when the left ventricle is rendered more clearly than the left atrium and the aorta are, there is a possibility that, if the transition had been made from the pre-scan to the main scan with timing later than the time T11, the contrast agent might have flowed out of the left ventricle to the aorta, so that the left ventricle could have been unclear in the acquired CT image data. Also, when the left ventricle is rendered more clearly than the left atrium and the aorta are, there is a possibility that, if the transition had been made from the pre-scan to the main scan with timing earlier than the time T11, the inflow of the contrast agent from the left atrium to the left ventricle might have been insufficient, so that the left ventricle could have been unclear in the acquired CT image data. Accordingly, when the left ventricle is rendered more clearly in the CT image data Ill than the left atrium and the aorta are, the learning function 352 is able to determine that the time T11 is "appropriate".

As explained above, when the operator plans to observe the left ventricle in the examination E11, the learning function 352 is able to acquire the information about appropriateness of the time T11, in accordance with how the left atrium, the left ventricle, and the aorta are contrast-enhanced in the CT image data Ill. In other words, on the basis of an examination purpose of the examination E11 and the CT image data Ill acquired in the examination E11, the learning function 352 is able to acquire the information about appropriateness of the time T11. In the following sections, an example will be explained in which "appropriate" has been acquired as the information about appropriateness of the time T11.

Similarly to the examination E11, the learning function 352 acquires information about appropriateness of the timing of transitions from a pre-scan to a main scan, with respect to a plurality of examinations. For example, in an examination E12 performed on the patient P11 that is different from the examination E11, the acquiring function 351 acquires a TDC, by plotting HU values in a region of interest in correspondence with a time axis, on the basis of a group of time-series image data acquired by performing a pre-scan on the patient P11 injected with a contrast agent.

Further, the determining function 353 determines a time T12 at which an HU value indicated in the TDC has reached the threshold value A11, as the timing of the transition from the pre-scan to the main scan in the examination E12. The TDC updated up to the time T12 in the examination E12 may be referred to as a TDC C12. Further, the X-ray CT apparatus 10 transitions from the pre-scan to the main scan at the time T12 and acquires CT image data 112. Further, on the basis of an examination purpose of the examination E11 and the CT image data 112 acquired in the examination E12, the learning function 352 acquires information "late" about appropriateness of the time T12.

Further, for example, in an examination E13 performed on a patient P12 different from the patient P11, the acquiring function 351 acquires a TDC by plotting HU values in a region of interest in correspondence with a time axis, on the basis of a group of time-series image data acquired by performing a pre-scan on the patient P12 injected with a contrast agent. The patient P12 is an example of the patient P illustrated in FIG. 2.

Further, the determining function 353 determines a time T13 at which an HU value indicated in the TDC has reached the threshold value A11, as the timing of the transition from the pre-scan to the main scan in the examination E13. The TDC updated up to the time T13 in the examination E13 may be referred to as a TDC C13. Further, the X-ray CT apparatus 10 transitions from the pre-scan to the main scan at the time T13 and acquires CT image data 113. Further, on the basis of an examination purpose of the examination E13 and the CT image data 113 acquired in the examination E13, the learning function 352 acquires information "early" about appropriateness of the time T13.

After that, the learning function 352 generates a trained model M1 used for determining appropriate timing of the transition from a pre-scan to a main scan, by using time-series information about the signal intensities in a region of interest generated on the basis of a group of time-series images acquired in a pre-scan and timing information about the timing of the transition from the pre-scan to a main scan as input-side learning data and using information about appropriateness of the timing of the transition from the pre-scan to the main scan as output-side learning data.

For example, the learning function 352 uses the TDC C11 acquired in the examination E11 and the timing information about the time T11 of the transition from the pre-scan to the main scan in the examination E11 as input-side learning data. The timing information about the time T11 is information directly or indirectly indicating the time T11. For example, the timing information may be the time representing the time T11. In the following sections, the timing information about the time T11 may simply be referred to as the time T11. In one example, as illustrated in FIG. 4A, as the timing information about the time T11, the learning function 352 acquires the time T11 at which any of the signal intensities in the region of interest of the patient P11 within the image data acquired in the pre-scan in the examination E11 exceeds the threshold value A11.

In other words, as illustrated in FIG. 4B, the learning function 352 uses the TDC C11 acquired in the examination E11 and the time T11 as the input-side learning data. Further, the learning function 352 uses the information "appropriate" about appropriateness of the time T11 acquired in the examination E11 as the output-side learning data. FIG. 4B is a table illustrating examples of the learning data used for generating the trained model M1 according to the first embodiment.

Further, the learning function 352 uses the TDC C12 acquired in the examination E11 and the time T12 of the transition from the pre-scan to the main scan in the examination E12, as input-side learning data. Further, the learning function 352 uses the information "late" about appropriateness of the time T12 acquired in the examination E12, as output-side learning data. Also, the learning function 352 uses the TDC C13 acquired in the examination E13 and the time T13 of the transition from the pre-scan to the main scan in the examination E13, as input-side learning data. Furthermore, the learning function 352 uses the information "early" about appropriateness of the time T13 acquired in the examination E13, as output-side learning data.

The trained model M1 may be structured with a neural network, for example. Neural networks are networks having a structure in which adjacent layers arranged in layers are linked together, so that information is propagated from the input-layer side to the output-layer side. For example, the learning function 352 generates the trained model M1 by using the learning data illustrated in FIG. 4B and performing deep learning on a multi-layer neural network. The multi-layer neural network may be structured, for example, with an input layer, a plurality of intermediate layers (hidden layers), and an output layer.

In one example, the learning function 352 inputs the input-side learning data illustrated in FIG. 4B to the neural network. In this situation, in the neural network, for example, information is propagated while only adjacent layers are linked together in one direction from the input-layer side toward the output-layer side, so that results of the categorization into the three classes of "early", "appropriate", and "late" are output from the output layer. Further, the learning function 352 adjusts parameters of the neural network so that the neural network is able to output desirable results, when the input-side learning data illustrated in FIG. 4B is input thereto.

For example, the learning function 352 adjusts the parameters of the neural network so as to eliminate inconsistency between outputs from the neural network and the output-side data illustrated in FIG. 4B. Accordingly, the learning function 352 is able to generate the trained model M1 functioned to receive an input of a TDC and timing and to output information indicating to which one of the classes among "early", "appropriate", and "late", the input timing corresponds. Further, the learning function 352 stores the generated trained model M1 into the model memory 34.

The neural network in which the information is propagated in one direction from the input-layer side toward the output-layer side may be referred to as a Convolutional Neural Network (CNN). The trained model M1 does not necessarily have to be structured with a convolutional neural network and may be structured with a neural network of another type.

In one example, the trained model M1 may be structured with a Recurrent Neural Network (RNN). In that situation, in the recurrent neural network, for example, not only information is propagated from the input-layer side toward the output-layer side, but also information output from an intermediate layer is re-input to another intermediate layer.

For example, the TDCs are sequentially updated during the pre-scans and are represented by data that chronologically changes. Further, the learning function 352 is capable of processing a TDC to generate a TDC corresponding to a point in time in the past. Thus, the learning function 352 may generate a trained model M1 by causing a recurrent neural network to learn information including such chronological changes of the TDC.

In one example, the TDC C11 illustrated in FIG. 4A is a TDC at the time T11. Further, by processing the TDC C11, the learning function 352 generates a TDC C111 at a time T111 earlier than the time T11 and another TDC C112 at a time T112 earlier than the time T111. In other words, the learning function 352 generates the plurality of TDCs that change chronologically.

After that, the learning function 352 inputs the plurality of TDCs that change chronologically, to the recurrent neural network. In this situation, in the recurrent neural network, information is propagated from the input-layer side toward the output-layer side, and also, for example, an output from an intermediate layer at the time of inputting the TDC C111 is input to an intermediate layer at the time of inputting the TDC C11. Also, an output from an intermediate layer at the time of inputting the TDC C111 is input to an intermediate layer at the time of inputting the TDC C112. In other words, in the recurrent neural network, an output from an intermediate layer in a certain temporal phase is fed back to an intermediate layer in another temporal phase.

Although the examples were explained in which the trained model M1 is structured with a neural network, possible embodiments are not limited to those examples. In other words, the learning function 352 may generate a trained model M1, by using a machine learning method other than neural networks. For example, the learning function 352 may generate a trained model M1 by using a machine learning method for categorizing data, such as a Support Vector Machine (SVM).

As explained above, the learning function 352 generates the trained model M1, by using the learning data acquired in the examination E11, the examination E12, the examination E13, or the like. In the following sections, among the examinations using the X-ray diagnostic system 1, an examination in which the learning data is acquired may be referred to as a first examination. In other words, the acquiring function 351 is configured to acquire a TDC generated on the basis of a group of time-series images acquired by performing a pre-scan on a patient injected with a contrast agent in the first examination. Further, the learning function 352 is configured to generate the trained model M1, by using the TDC acquired by the acquiring function 351 and the timing information about the timing of the transition from the pre-scan to the main scan in the first examination as the input-side learning data and using the information about appropriateness of the timing of the transition from the pre-scan to the main scan in the first examination as the output-side learning data.

Further, by using the trained model M1, the determining function 353 is configured to determine appropriate timing of the transition from the pre-scan to the main scan in an examination different from the first examination. The examination in which the trained model M1 is used may be referred to as a second examination. In other words, the learning function 352 is configured to generate the trained model M1 used for determining the appropriate timing of the transition from the pre-scan to the main scan in the second examination different from the first examination. The determining function 353 is configured to determine, in the second examination, the appropriate timing of the transition from the pre-scan to the main scan, by using the trained model M1.

Figure 5A:
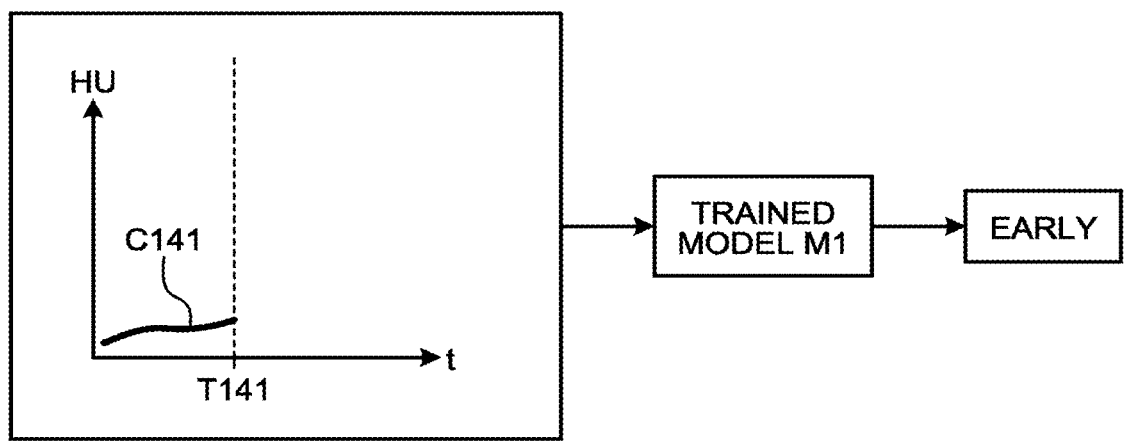
FIG. 5A is a diagram illustrating an example of use of the trained model according to the first embodiment.
Figure 5B:
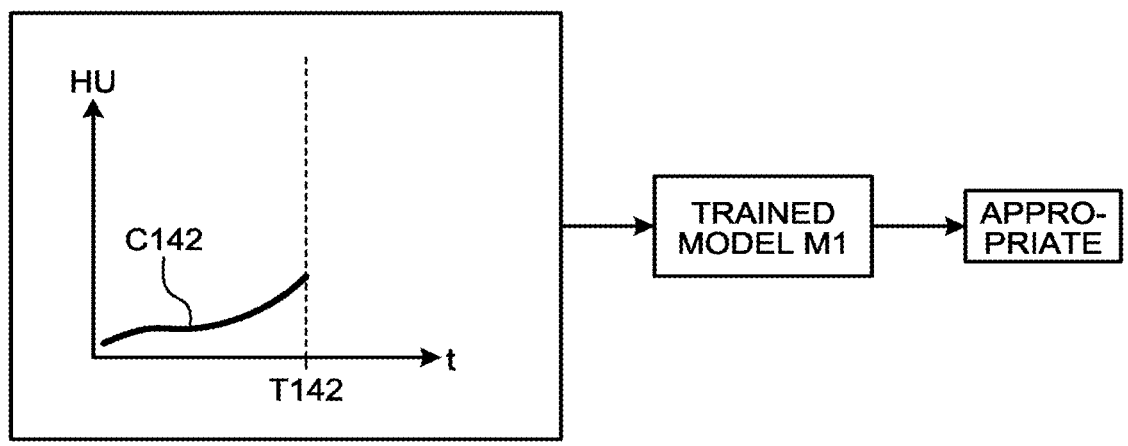
FIG. 5B is a diagram illustrating another example of the use of the trained model according to the first embodiment.

Next, examples of use of the trained model M1 will be explained, with reference to FIGS. 5A and 5B. FIGS. 5A and 5B are diagrams illustrating the examples of the use of the trained model M1 according to the first embodiment. With reference to FIGS. 5A and 5B, the examples will be explained in which, in an examination E14 performed on a patient P13 different from the patient P11 and the patient P12, appropriate timing of the transition from the pre-scan to the main scan is determined by using the trained model M1. The patient P13 is an example of the patient P illustrated in FIG. 2. The examination E14 is an example of the second examination.

In the examination E14, at first, the system controlling function 144a sets a target site of the main scan and a target site of the pre-scan. In the following sections, an example will be explained in which the target site of the main scan in the examination E14 is the "heart", whereas the target site of the pre-scan in the examination E14 is the "aorta". Subsequently, the system controlling function 144a performs the pre-scan on the "aorta" of the patient P13 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs pre-processing processes on the projection data output from the DAS 118. Further, the generating function 144c sequentially generates image data on the basis of the projection data on which the pre-processing processes have been performed. Further, the controlling function 144d sequentially transmits the generated image data to the medical information processing apparatus 30. Further, the acquiring function 351 sequentially acquires the transmitted image data. Also, the acquiring function 351 sets a region of interest of the patient P13.

Subsequently, the acquiring function 351 acquires a TDC on the basis of signal intensities in the region of interest within the group of time-series image data acquired in the pre-scan. For example, the acquiring function 351 acquires the TDC by plotting HU values in the region of interest in correspondence with a time axis, with respect to the pieces of image data in the group of time-series image data. Further, every time image data is newly acquired from the X-ray CT apparatus 10, the acquiring function 351 sequentially updates the TDC, by plotting the HU values in the region of interest in the newly-acquired image data in correspondence with the time axis. The TDC updated up to a time T141 in FIG. 5A will hereinafter be referred to as a TDC C141. Also, the TDC updated up to a time T142 in FIG. 5B will hereinafter be referred to as a TDC C142.

In this situation, the determining function 353 sequentially inputs the acquired TDCs to the trained model M1. For example, at the time T141, the determining function 353 inputs the TDC C141 illustrated in FIG. 5A to the trained model M1. In this situation, upon receiving the input of the TDC C141 and the time T141, the trained model M1 outputs information indicating to which one of the classes among "early", "appropriate", and "late", the time T141 corresponds. FIG. 5A illustrates an example in which the trained model M1 outputs "early". In that situation, the determining function 353 determines that the time T141 is not appropriate timing of the transition from the pre-scan to the main scan.

Further, for example, at the time T142, the determining function 353 inputs the TDC C142 illustrated in FIG. 5B to the trained model M1. In this situation, upon receiving the input of the TDC C142 and the time T142, the trained model M1 outputs information indicating to which one of the classes among "early", "appropriate", and "later", the time T142 corresponds. FIG. 5B illustrates an example in which the trained model M1 outputs "appropriate". In that situation, the determining function 353 determines that the time T142 is appropriate timing of the transition from the pre-scan to the main scan.

Further, the controlling function 354 transmits the determined time T142 to the X-ray CT apparatus 10. Further, the X-ray CT apparatus 10 transitions from the pre-scan to the main scan at the time T142 and acquires CT image data 114 (not illustrated). In other words, the X-ray CT apparatus 10 transitions from the pre-scan to the main scan at the time T142 determined by using the trained model M1 and acquires the CT image data 114. As a result of the transition to the main scan, the pre-scan ends, and the updating of the TDC also ends.

In this situation, when the trained model M1 is used, there is no need to set the threshold value A11 illustrated in FIG. 3, to determine the timing of the transition from the pre-scan to the main scan. Further, by using the trained model M1, it is possible to determine, with a high level of precision, the timing of the transition from the pre-scan to the main scan, while evaluating not only simply the magnitudes of the HU values in the region of interest, but also changes in the HU values over the course of time (i.e., the shape of the TDC). Consequently, the X-ray diagnostic system 1 according to the first embodiment is able to appropriately determine the timing of the main scan, by using the trained model M1.

Further, the learning function 352 may generate a trained model M1, by using the learning data acquired in the examination E14. In other words, the learning function 352 may update the trained model M1, by using the learning data acquired in the examination E14. For example, the learning function 352 acquires information about appropriateness of the time T142, on the basis of an examination purpose of the examination E14 and the CT image data 114 acquired in the examination E14. Further, the learning function 352 updates the trained model M1, by using the TDC C142 illustrated in FIG. 5B and the time T142 of the transition from the pre-scan to the main scan in the examination E14 as input-side learning data and using information about appropriateness of the time T142 as output-side learning data.

In other words, after using the trained model M1 with respect to the examination E14, the learning function 352 acquires the learning data from the examination E14. In that situation, the examination E14 corresponds to both the first examination and the second examination. Further, by updating the trained model M1 with the learning data acquired in the examination E14, the learning function 352 makes it possible to determine the timing of the main scan more appropriately, by enhancing the level of precision of the trained model M1. In other words, in the X-ray diagnostic system 1, as a result of repeatedly performing the examinations that each include a pre-scan and a main scan, it becomes gradually possible to determine the timing of a main scan more appropriately.

Further, the learning function 352 may generate a plurality of pieces of learning data on the basis of the learning data acquired from one examination. In the following sections, an example of an examination E15 performed on a patient P14 will be explained. The patient P14 is an example of the patient P illustrated in FIG. 2. For example, the learning function 352 acquires, from the examination E15, a TDC 15 acquired in the examination E15, a time T15 of the transition from the pre-scan to the main scan in the examination E15, and information "late" about appropriateness of the time T15, as learning data. After that, on the basis of the learning data structured with the set made up of the TDC 15, the time T15, and the information "late" about appropriateness of the time T15, the learning function 352 generates a plurality of pieces of learning data.

Figure 6A:
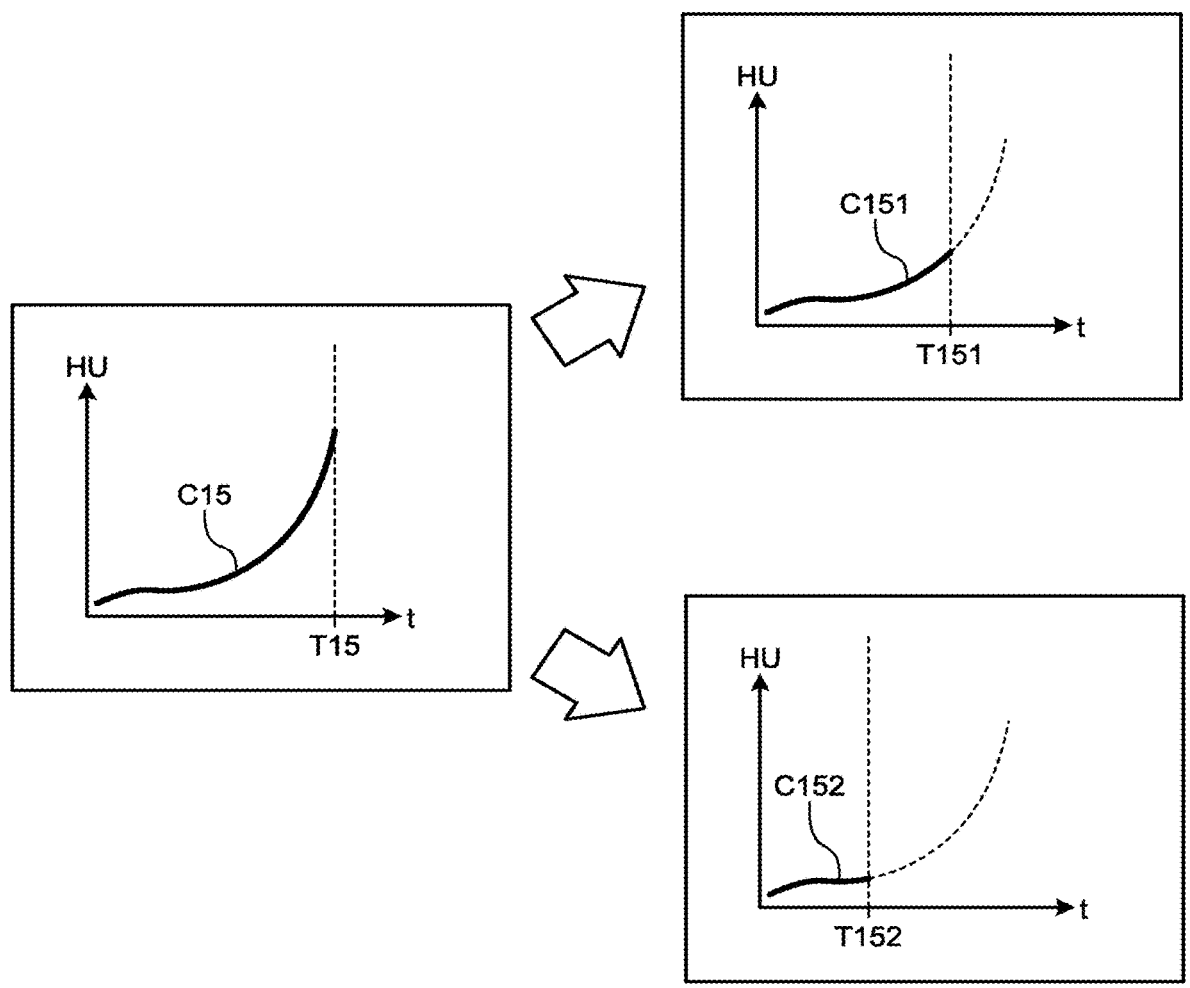
FIG. 6A is a drawing for explaining a process of generating the learning data used for generating the trained model according to the first embodiment.

For example, as illustrated in FIG. 6A, the learning function 352 generates a TDC C151 at a time T151 earlier than the time T15 and another TDC C152 at a time T152 earlier than the time T151, by processing the TDC 15, which is a TDC updated up to the time T15. Accordingly, on the basis of the set made up of the TDC 15, the time T15, and the information "late" about appropriateness of the time T15, the learning function 352 generates a set made up of the TDC C151, the time T151, and information "appropriate" about appropriateness of the time T151 and another set made up of the TDC C152, the time T152, and information "early" about appropriateness of the time T152. FIG. 6A is a drawing for explaining the process of generating the learning data used for generating the trained model M1 according to the first embodiment.

For example, as illustrated in FIG. 6B, in addition to the set made up of the TDC 15, the time T15, and the information "late" about appropriateness of the time T15, the learning function 352 generates a trained model M1 by further using the set made up of the TDC C151, the time T151, and the information "appropriate" about appropriateness of the time T151 and the set made up of the TDC C152, the time T152, and the information "early" about appropriateness of the time T152, as input-side and output-side learning data. FIG. 6B is a drawing illustrating the examples of the learning data used for generating the trained model M1 according to the first embodiment.

In the example illustrated in FIG. 6B, the learning function 352 is configured to generate the trained model M1 on the basis of the three pieces of learning data acquired in the examination E15. Further, by performing the machine learning while using the larger number of pieces of learning data, the learning function 352 makes it possible to determine the timing of the main scan more appropriately, by enhancing the level of precision of the trained model M1.

As for the time T151 corresponding to "appropriate", it is possible to calculate the time on the basis of, for example, the CT image data 115 acquired in the examination E15. For example, from the CT image data 115, the learning function 352 acquires shape data of the target site "heart" of the main scan and a distribution of the contrast agent. Subsequently, the learning function 352 performs a fluid simulation by using the shape data of the "heart" and the distribution of the contrast agent as constraint conditions and further estimates the CT image data that would have been acquired if the transition to the main scan had been made earlier than the time T15. After that, on the basis of the estimated CT image data and an examination purpose of the examination E15, the learning function 352 calculates the time T151 corresponding to "appropriate".

Alternatively, the learning function 352 may calculate a time period corresponding to "appropriate" and may determine an arbitrary time included in the calculated time period as the time T151. For example, when the operator plans to observe the left ventricle of the patient P15 in the examination E15, the learning function 352 determines, from within the CT image data estimated from the fluid simulation, CT image data in which the left atrium is recognizable to be "appropriate". In this situation, when there are a plurality of pieces of CT image data in which the left atrium is recognizable, the learning function 352 calculates the time period corresponding to the plurality of pieces of CT image data as a time period corresponding to "appropriate" and determines an arbitrary time included in the calculated time period as the time T151.

Further, FIG. 6B illustrates only the one piece of learning data including the information "early" about appropriateness; however, the learning function 352 may select a plurality of points in time earlier than the time T151 corresponding to "appropriate", so as to generate a plurality of pieces of learning data each including information "early" about appropriateness. Alternatively, when having calculated the time period corresponding to "appropriate", the learning function 352 may select a plurality of points in time included in the calculated time period, so as to generate a plurality of pieces of learning data each including information "appropriate" about appropriateness.

Figure 7:
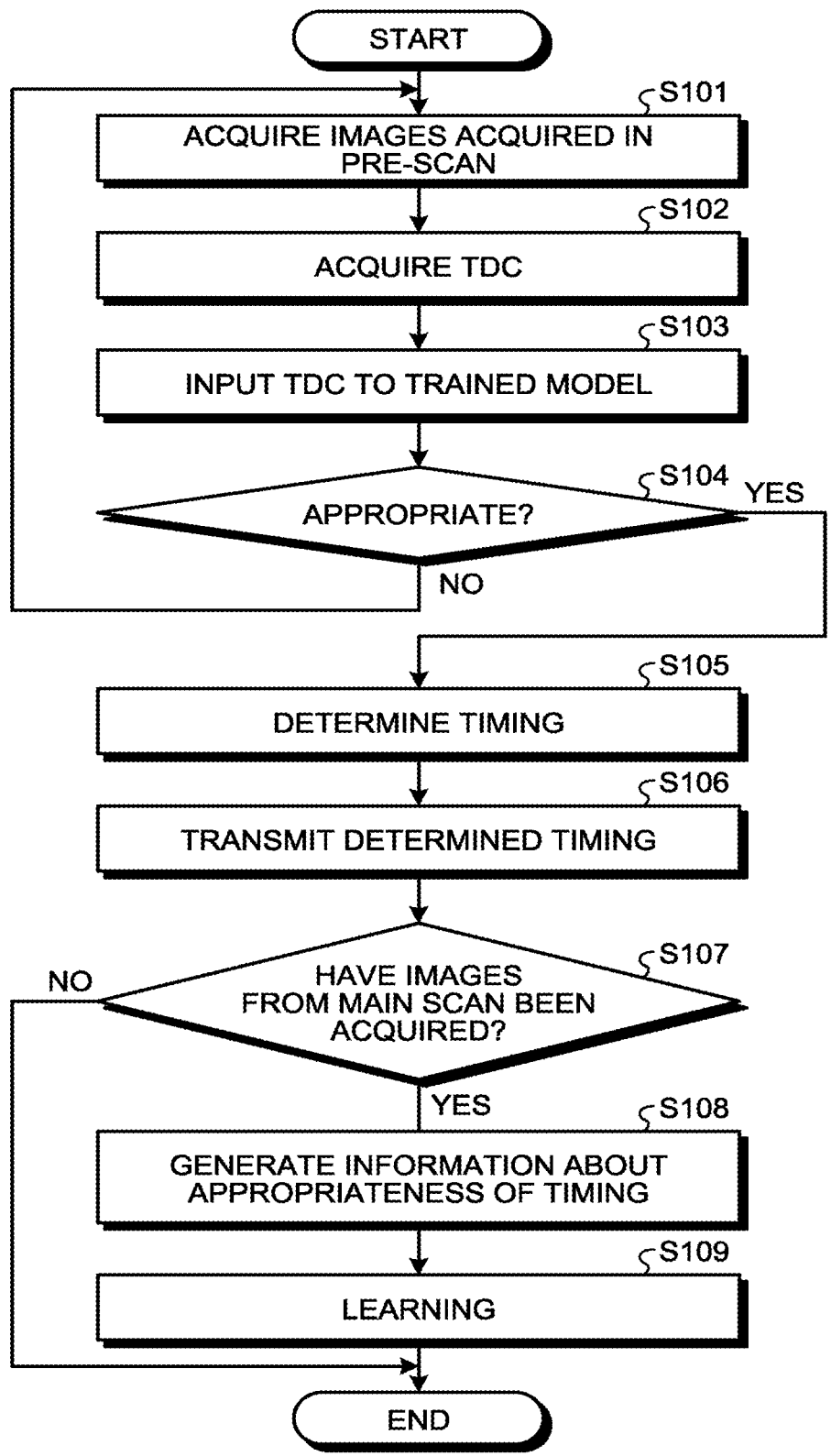
FIG. 7 is a flowchart for explaining a flow in a series of processes performed by the X-ray diagnostic system according to the first embodiment.

Next, an example of a procedure in processes performed by the X-ray diagnostic system 1 will be explained with reference to FIG. 7. FIG. 7 is a flowchart for explaining a flow in the series of processes performed by the X-ray diagnostic system 1 according to the first embodiment.

Steps S101, S102, and S107 are steps corresponding to the acquiring function 351. Steps S108 and S109 are steps corresponding to the learning function 352. Steps S103, S104, and S105 are steps corresponding to the determining function 353. Step S106 is a step corresponding to the controlling function 354.

At first, the processing circuitry 35 acquires image data acquired by performing a pre-scan on the patient P injected with a contrast agent, from the X-ray CT apparatus (step S101) and acquires a TDC on the basis of the acquired image data (step S102). Subsequently, the processing circuitry 35 inputs the acquired TDC to the trained model M1 (step S103).

In this situation, the processing circuitry 35 judges whether or not the output of the trained model M1 is "appropriate" (step S104). When the output is not "appropriate" (step S104: No), the process returns to step S101. On the contrary, when the output of the trained model M1 is "appropriate" (step S104: Yes), the processing circuitry 35 determines timing of the transition from the pre-scan to the main scan (step S105) and transmits the determined timing to the X-ray CT apparatus 10 (step S106). Further, not only when the output of the trained model M1 is "appropriate", the processing circuitry 35 may determine the timing of the transition from the pre-scan to the main scan, also when the output of the trained model M1 is "late".

Subsequently, the processing circuitry 35 judges whether or not the CT image data acquired in the main scan has been acquired from the X-ray CT apparatus 10 (step S107). When the CT image data has been acquired (step S107: Yes), the processing circuitry 35 acquires information about appropriateness of the timing determined at step S105, on the basis of the CT image data and an examination purpose (step S108). After that, the processing circuitry 35 generates a trained model M1 by using the TDC acquired at step S102 and the timing determined at step S105 as input-side learning data and using the information about appropriateness acquired at step S108 as output-side learning data (step S109) and the process is ended. Further, when no CT image data has been acquired from the X-ray CT apparatus 10 (e.g., when the main scan was cancelled), the processing circuitry 35 also ends the process.

As explained above, according to the first embodiment, the acquiring function 351 acquires the TDC generated on the basis of the group of time-series image data acquired by performing the pre-scan on the patient P injected with the contrast agent, in the first examination using the X-ray diagnostic system 1. Further, the learning function 352 generates the trained model M1 used for determining appropriate timing of the transition from the pre-scan to the main scan in the second examination, by using the TDC acquired by the acquiring function 351 and the timing information about the timing of the transition from the pre-scan to the main scan in the first examination as the input-side learning data and using the information about appropriateness of the timing of the transition from the pre-scan to the main scan in the first examination as the output-side learning data. Consequently, the X-ray diagnostic system 1 according to the first embodiment is able to appropriately determine the timing of the main scan, by using the trained model M1.

Further, as explained above, according to the first embodiment, as the information about appropriateness, the learning function 352 uses the information indicating to which one of the classes among "appropriate", "early", and "late", the timing of the transition from the pre-scan to the main scan in the first examination corresponds. In other words, as the information about appropriateness, the learning function 352 uses the information indicating to which one of the options the timing of the transition from the pre-scan to the main scan in the first examination corresponds, the options namely being: highly appropriate timing, timing earlier than the highly appropriate timing, and timing later than the highly appropriate timing. Consequently, the X-ray diagnostic system 1 according to the first embodiment is able to easily acquire the information about appropriateness and to promptly generate the trained model M1 by keeping the problem solved by the trained model M1 simple.

Further, as explained above, according to the first embodiment, in addition to the set made up of the TDC 15, the time T15, and the information "late" about appropriateness of the time T15, the learning function 352 generates the trained model M1 by further using the set made up of the TDC C151, the time T151, and the information "appropriate" about appropriateness of the time T151 and the set made up of the TDC C152, the time T152, and the information "early" about appropriateness of the time T152, as the input-side and the output-side learning data. In other words, on the basis of the set made up of the information indicating that the timing of the transition from the pre-scan to the main scan in the first examination corresponds to timing later than the highly appropriate timing, the TDC generated on the basis of the group of time-series image data acquired in the pre-scan performed in the first examination, and the timing information about the timing of the transition from the pre-scan to the main scan in the first examination, the learning function 352 generates at least one selected from between: (i) the set made up of the information indicating that the timing of the transition from the pre-scan to the main scan in the first examination corresponds to the highly appropriate timing, the TDC acquired by processing the TDC generated on the basis of the group of time-series image data acquired in the pre-scan performed in the first examination, and the timing information acquired by processing the timing information about the timing of the transition from the pre-scan to the main scan in the first examination; and (ii) the set made up of the information indicating that the timing of the transition from the pre-scan to the main scan in the first examination corresponds to timing earlier than the highly appropriate timing, the TDC acquired by processing the TDC generated on the basis of the group of time-series image data acquired in the pre-scan performed in the first examination, and the timing information acquired by processing the timing information about the timing of the transition from the pre-scan to the main scan in the first examination, and generates the trained model M1 by further using the generated set as the input-side and the output-side learning data. Consequently, by performing the machine learning while using the larger number of pieces of learning data, the X-ray diagnostic system 1 according to the first embodiment is able to determine the timing of the main scan more appropriately, by enhancing the level of precision of the trained model M1.

The examples have been explained in which the target site of the main scan is the "heart", whereas the target site of the pre-scan is the "aorta"; however, possible embodiments are not limited to this example. It is possible to arbitrarily change the combination of the target site of the main scan and the target site of the pre-scan. As one example, the present disclosure is similarly applicable to a situation where the target site of the main scan is the "head", whereas the target site of the pre-scan is a "carotid artery". As another example, the present disclosure is similarly applicable to a situation where the target site of the main scan is the "abdomen", whereas the target site of the pre-scan is the "aorta". As yet another example, the present disclosure is similarly applicable to a situation where the target site of the main scan is the "liver", whereas the target site of the pre-scan is the "portal phase".

In this situation, the learning function 352 may generate a trained model M1 with respect to each target site. For example, the learning function 352 generates a trained model M1 with respect to each set made up of the target site of a main scan and the target site of a pre-scan and stores the plurality of generated trained models M1 into the model memory 34. Further, in the second examination, the determining function 353 reads one of the trained models M1 in accordance with the target site of the main scan and the target site of the pre-scan and determines appropriate timing of the transition from the pre-scan to the main scan in the second examination, by using the read trained model M1. In that situation, by performing the machine learning specialized for each target site, the X-ray diagnostic system 1 is able to determine the timing of the main scan more appropriately, by enhancing the level of precision of the trained model M1.

Further, the learning function 352 may generate the trained model M1 in accordance with the injection position of the contrast agent. For example, when the target site of the main scan is the "heart", the contrast agent may be injected through a vein in the right arm of the patient P or may be injected through a vein in the left arm of the patient P. In this regard, between the situation where the contrast agent is injected through the vein in the right arm and the situation where the contrast agent is injected through the vein in the left arm, because the paths of the contrast agent to reach the heart are different, there is a possibility that the appropriate timing of the main scan may vary.

For example, the learning function 352 generates trained models M1 for the "right arm" and for the "left arm" serving as injection positions of the contrast agent and further stores the plurality of generated trained models M1 into the model memory 34. Further, in the second examination, the determining function 353 reads one of the trained models M1 in accordance with the injection position of the contrast agent and determines appropriate timing of the transition from the pre-scan to the main scan in the second examination, by using the read trained model M1. In that situation, the X-ray diagnostic system 1 is able to determine the timing of the main scan more appropriately, by using the trained model M1 specialized for each of the injection positions of the contrast agent.

Alternatively, the learning function 352 may generate a single trained model M1 by using the "right arm" and the "left arm" serving as the injection positions of the contrast agent as input-side learning data and store the generated trained model M1 into the model memory 34. Further, in the second examination, the determining function 353 determines appropriate timing of the transition from the pre-scan to the main scan in the second examination by inputting input data including the injection position of the contrast agent to the trained model M1. In that situation, the X-ray diagnostic system 1 is able to determine the timing of the main scan more appropriately, by using the trained model M1 that has learned impacts of the injection positions of the contrast agent.

Further, the learning function 352 may generate the trained model M1 in accordance with information (patient's background) about the patient P. For example, when the patient P has a disease in the "heart", there is a tendency that it takes a longer period of time for the contrast agent to reach the target site of the main scan, after being injected. Further, there are differences in the blood flow speed depending on the age, the height, the weight, the gender, and the like of the patient P. As a result, the time it takes for the contrast agent to reach the target site of the main scan after being injected may vary.

For example, the learning function 352 may categorize each of the patients P into one of a plurality of groups according to the patient's background, generate a trained model M1 for each of the plurality of groups, and stores the plurality of generated trained models M1 into the model memory 34. Further, in the second examination, the determining function 353 reads one of the trained models M1 in accordance with the patient's background and determines appropriate timing of the transition from the pre-scan to the main scan in the second examination by using the read trained model M1. In that situation, the X-ray diagnostic system 1 is able to determine the timing of the main scan more appropriately, by using the trained model M1 specialized for each patient's background.

Alternatively, the learning function 352 may generate a single trained model M1 by using patients' backgrounds as input-side learning data and store the generated trained model M1 into the model memory 34. After that, in the second examination, the determining function 353 determines appropriate timing of the transition from the pre-scan to the main scan in the second examination, by inputting input data including the patient's background to the trained model M1. In that situation, the X-ray diagnostic system 1 is able to determine the timing of the main scan more appropriately, by using the trained model M1 that has learned impacts of the patients' backgrounds.

Further, the examples have been explained in which the acquiring function 351 acquires the group of time-series image data from the X-ray CT apparatus 10, sets the region of interest, and acquires the TDC by plotting the HU values in the region of interest in correspondence with the time axis on the basis of the group of time-series image data; however, possible embodiments are not limited to this example. For instance, the acquiring function 351 may acquire a TDC generated by the X-ray CT apparatus 10 from the X-ray CT apparatus 10.

Further, the acquiring function 351 may generate a TDC on the basis of a region of interest set by the X-ray CT apparatus 10. For example, the acquiring function 351 may acquire a group of data corresponding to the region of interest and being generated by the X-ray CT apparatus 10 on the basis of a group of time-series image data and may further acquire the TDC by plotting the HU values in the region of interest in correspondence with a time axis on the basis of the acquired group of data.

The group of time-series data corresponding to the region of interest and being generated on the basis of the group of time-series image data may be referred to as a group of partial image data. The partial image data may be data acquired by adding position information of the region of interest to image data or may be data acquired by cutting out a part corresponding to the region of interest from image data. For example, the acquiring function 351 may acquire the group of time-series partial image data from the X-ray CT apparatus 10 and may further acquire a TDC on the basis of the acquired group of time-series partial image data.

Further, the TDC has been explained as the time-series information about the signal intensities in the region of interest of the patient P generated on the basis of the group of time-series image data acquired in the pre-scan; however, possible embodiments are not limited to this example. For instance, in place of the TDC, the acquiring function 351 may acquire numerical value data indicating, in a time series, the HU values in the region of interest.

Figure 8:
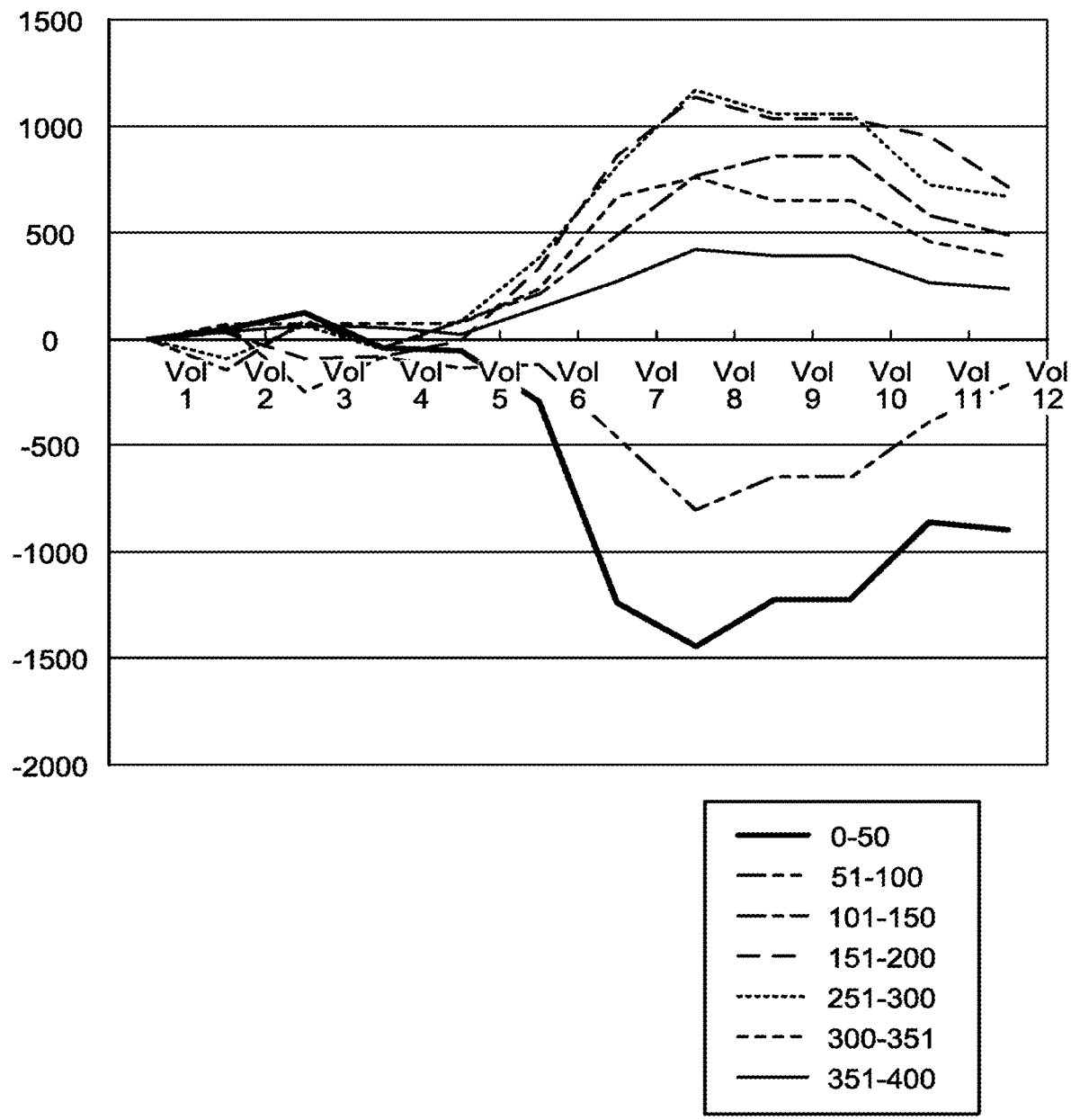
FIG. 8 is a drawing for explaining information about a specific signal value band according to the first embodiment.

In another example, as the time-series information about the signal intensities in the region of interest of the patient P, the acquiring function 351 may use information about a specific signal value band. In the following sections, this example will be explained, with reference to FIG. 8. FIG. 8 is a drawing for explaining the information about the specific signal value band according to the first embodiment.

The labels "Vol. 1" to "Vol. 12" on the horizontal axis in FIG. 8 denote image numbers of pieces of image data acquired in a time series. In other words, the horizontal axis in FIG. 8 corresponds to a time axis. The vertical axis in FIG. 8 expresses frequency of occurrence (hereinafter, simply "frequency") related to the number of pixels. More specifically, the vertical axis in FIG. 8 expresses the frequency by using "Vol. 1" as a reference, with respect to the number of pixels of each of which the CT value falls in the range of "0 to 50"; the number of pixels of each of which the CT value falls in the range of "51 to 100"; the number of pixels of each of which the CT value falls in the range of "101 to 150"; the number of pixels of each of which the CT value falls in the range of "151 to 200"; the number of pixels of each of which the CT value falls in the range of "251 to 300"; the number of pixels of each of which the CT value falls in the range of "301 to 350"; and the number of pixels of each of which the CT value falls in the range of "351 to 400".

When a contrast agent is injected, as illustrated in FIG. 8, the frequency of pixels of each of which the CT value falls in the range of "151 to 200" increases. In other words, when the contrast agent is injected, the frequency of the signal value band corresponding to the contrast agent increases. Accordingly, as the information about the specific signal value band, the learning function 352 acquires the frequency of pixels of each of which the CT value falls in the range of "151 to 200". As the frequency of pixels of each of which the CT value falls in the range of "151 to 200", the learning function 352 may acquire the graph as illustrated in FIG. 8 or may acquire numerical value data kept in correspondence with the image numbers or time. Further, the learning function 352 generates a trained model, by using the frequency of pixels of each of which the CT value falls in the range of "151 to 200", as learning data.

Although the example was explained in which the frequency of pixels of each of which the CT value falls in the range of "151 to 200" is used as the learning data, the learning function 352 may further use the frequency of pixels of each of which the CT value falls in the range of "251 to 300" as learning data. In other words, the acquiring function 351 may use the information about the plurality of signal value bands. Further, as illustrated in FIG. 8, when a contrast agent is injected, while the frequency of the signal value band corresponding to the contrast agent increases, the frequency of the other signal value bands (e.g., the CT value "0 to 50") decreases. Accordingly, the learning function 352 may use the frequency of pixels of each of which the CT value falls in the range of "0 to 50" as learning data.

Further, with reference to FIG. 4A, the time at which any of the signal intensities in the region of interest exceeds the threshold value was explained as the timing of the transition from the pre-scan to the main scan; however, possible embodiments are not limited to this example. For instance, the determining function 353 may determine a time when a predetermined period of time has elapsed since the time at which any of the signal intensities in the region of interest exceeded a threshold value, as the timing of the transition from the pre-scan to the main scan. In that situation, the learning function 352 acquires the time when the predetermined period of time has elapsed since any of the signal intensities in the region of interest exceeded the threshold value, as the timing information about the timing of the transition from the pre-scan to the main scan.

In the first embodiment above, the information about appropriateness was explained with the example of the information indicating to which one of the options the timing of the transition from the pre-scan to the main scan in the first examination corresponds, the options namely being: highly appropriate timing, timing earlier than the highly appropriate timing, and timing later than the highly appropriate timing. In contrast, in a second embodiment, as an example of the information about appropriateness, a difference between the timing of the transition from the pre-scan to the main scan in the first examination and the highly appropriate timing will be explained.

The X-ray diagnostic system 1 according to the second embodiment has the same configuration as that of the X-ray diagnostic system 1 illustrated in FIGS. 1 and 2, while parts of the processes performed by the learning function 352 and the determining function 353 are different. In the following sections, some of the constituent elements having the same configurations as those explained in the first embodiment will be referred to by using the same reference characters as those in FIGS. 1 and 2, and the explanations thereof will be omitted.

Next, an example will be explained in which learning data is acquired in an examination E21 performed on a patient P21, with reference to FIG. 9A. The patient P21 is an example of the patient P illustrated in FIG. 2. Further, FIG. 9A a drawing illustrating an example of a learning data acquiring process according to the second embodiment.

In the examination E21, at first, the system controlling function 144a sets a target site of the main scan and a target site of the pre-scan. In the following sections, an example will be explained in which the target site of the main scan in the examination E21 is the "heart", whereas the target site of the pre-scan in the examination E21 is the "aorta". Subsequently, the system controlling function 144a performs the pre-scan on the "aorta" of the patient P21 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs the pre-processing processes on the projection data output from the DAS 118. Further, the generating function 144c sequentially generates image data on the basis of the projection data on which the pre-processing processes have been performed. Further, the controlling function 144d sequentially transmits the generated image data to the medical information processing apparatus 30. Further, the acquiring function 351 sequentially acquires the transmitted image data. Also, the acquiring function 351 sets a region of interest of the patient P21.

Subsequently, the acquiring function 351 acquires a TDC on the basis of signal intensities in the region of interest within the group of time-series image data acquired in the pre-scan. For example, the acquiring function 351 acquires the TDC by plotting HU values in the region of interest in correspondence with a time axis, with respect to the pieces of image data in the group of time-series image data. Further, every time image data is newly acquired from the X-ray CT apparatus 10, the acquiring function 351 sequentially updates the TDC, by plotting the HU values in the region of interest in the newly-acquired image data in correspondence with the time axis. In the following sections, the TDC updated up to a time T21 in FIG. 9A will be referred to as a TDC C21.

With reference to FIG. 9A, an example will be explained in which the time T21 is determined as the timing of the transition from the pre-scan to the main scan. In FIG. 9A, the determining function 353 may determine the time T21 by using the threshold value A11, may determine the time T21 by using the trained model M1, or may determine the time T21 by using a trained model M2 (explained later).

After that, the determining function 353 identifies highly appropriate timing, which is a time Tv21. In this situation, the highly appropriate timing, i.e., the time Tv21 is, for example, optimal timing as the timing of the transition from the pre-scan to the main scan in the examination E21. For example, the determining function 353 identifies the highly appropriate timing, i.e., the time Tv21, on the basis of an examination purpose of the examination E21 and CT image data 121 acquired in the examination E21.

For example, from the CT image data 121, the learning function 352 acquires shape data of the "heart" serving as the target site of the main scan and a distribution of the contrast agent. Subsequently, the learning function 352 performs a fluid simulation by using the shape data of the "heart" and the distribution of the contrast agent as constraint conditions and estimates CT image data that would have been acquired if the transition to the main scan had been made earlier than the time T21 and CT image data that would have been acquired if the transition to the main scan had been made later than the time T21. Further, on the basis of the estimated CT image data and an examination purpose of the examination E21, the learning function 352 identifies the highly appropriate timing, i.e., the time Tv21.

In one example, when the operator plans to observe the left ventricle of the patient P21 in the examination E21, the learning function 352 identifies, from within the CT image data 121 and the estimated CT image data, CT image data in which the left atrium is rendered most clearly. Further, the learning function 352 identifies the timing corresponding to the identified CT image data as the highly appropriate timing, i.e., the time Tv21.

Subsequently, the learning function 352 calculates the difference between the highly appropriate timing, i.e., the Tv21, and the time T21 of the transition from the pre-scan to the main scan in the examination E21. For example, as the difference between the time Tv21 and the time T21, the learning function 352 calculates "+1.5 seconds". The notation "+1.5 seconds" indicates that the time T21 is 1.5 seconds later than the highly appropriate timing, i.e., the time Tv21. In other words, the notation "+1.5 seconds" indicates that optimal CT image data could have been acquired if the transition to the main scan had been made 1.5 seconds earlier in the examination E21.

With respect to a plurality of examinations, the learning function 352 calculates the difference between the timing of the transition from the pre-scan to the main scan and highly appropriate timing, similarly to the calculation for the examination E21. For example, in an examination E22 different from the examination E21, the acquiring function 351 acquires a TDC by plotting HU values in the region of interest in correspondence with a time axis, on the basis of a group of time-series image data acquired by performing a pre-scan on a patient P22 injected with a contrast agent. The patient P22 is an example of the patient P illustrated in FIG. 2. Further, the determining function 353 determines a time T22 as the timing of the transition from the pre-scan to the main scan in the examination E22 and further acquires a TDC C22 updated up to the time T22. Further, the learning function 352 identifies highly appropriate timing for the examination E22, which is a time Tv22, on the basis of an examination purpose of the examination E22 and CT image data 122 acquired in the examination E22. Further, the learning function 352 calculates the difference between the highly appropriate timing, i.e., the time Tv22, and the time T22 of the transition from the pre-scan to the main scan in the examination E22.

For example, the learning function 352 calculates "0 seconds" as the difference between the time Tv22 and the time T22. The notation "0 seconds" indicates that the time T22 coincides with the highly appropriate timing, the time Tv22. In other words, the notation "0 seconds" indicates that the CT image data 122 acquired in the examination E22 is optimal CT image data.

Further, for example, in an examination E23 different from the examinations E21 and E22, the acquiring function 351 acquires a TDC by plotting HU values in the region of interest in correspondence with a time axis, on the basis of a group of time-series image data acquired by performing a pre-scan on a patient P injected with a contrast agent. The patient P23 is an example of the patient P illustrated in FIG. 2. Further, the determining function 353 determines a time T23 as the timing of the transition from the pre-scan to the main scan in the examination E23 and further acquires a TDC C23 updated up to the time T23. Further, the learning function 352 identifies highly appropriate timing for the examination E23, which is a time Tv23, on the basis of an examination purpose of the examination E23 and CT image data 123 acquired in the examination E23. Further, the learning function 352 calculates the difference between the highly appropriate timing, i.e., the time Tv23, and the time T23 of the transition from the pre-scan to the main scan in the examination E23.

For example, the learning function 352 calculates "−1 seconds" as the difference between the time Tv23 and the time T23. The notation "−1 seconds" indicates that the time T23 is 1 second earlier than the highly appropriate timing, i.e., the time Tv23. In other words, the notation "−1 seconds" indicates that optimal CT image could have been acquired if the transition to the main scan had been made 1 second later in the examination E23.

Subsequently, the learning function 352 generates the trained model M2 used for determining appropriate timing of the transition from the pre-scan to the main scan, by using time-series information about the signal intensities in the region of interest generated on the basis of the group of time-series images acquired in the pre-scan and timing information about the timing of the transition from the pre-scan to the main scan as input-side learning data and using the information about appropriateness of the timing of the transition from the pre-scan to the main scan as output-side learning data.

For example, as illustrated in FIG. 9B, the learning function 352 uses the TDC C21 acquired in the examination E21 and the time T21 of the transition from the pre-scan to the main scan in the examination E21 as the input-side learning data. Further, the learning function 352 uses the difference "+1.5 seconds" between the time Tv21 and the time T21 that was acquired in the examination E21, as the output-side learning data. FIG. 9B is a drawing illustrating the examples of the learning data used for generating the trained model M2 according to the second embodiment.

Further, the learning function 352 uses the TDC C22 acquired in the examination E22 and the time T22 of the transition from the pre-scan to the main scan in the examination E22 as the input-side learning data. Further, the learning function 352 uses the difference "0 seconds" between the time Tv22 and the time T22 that was acquired in the examination E22, as the output-side learning data. Further, the learning function 352 uses the TDC C23 acquired in the examination E23 and the time T23 of the transition from the pre-scan to the main scan in the examination E23 as the input-side learning data. Further, the learning function 352 uses the difference "−1 second" between the time Tv23 and the time T23 that was acquired in the examination E23, as the output-side learning data.

For example, the learning function 352 generates the trained model M2, by performing deep learning on a multi-layer neural network while using the learning data illustrated in FIG. 9B. In one example, the learning function 352 inputs the input-side learning data illustrated in FIG. 9B to the neural network. In this situation, for example, in the neural network, information is propagated while only adjacent layers are linked together in one direction from the input-layer side toward the output-layer side, so that the difference between input timing and highly appropriate timing is output from the output layer. Further, the learning function 352 adjusts parameters of the neural network so that the neural network is able to output desirable results when the input-side learning data illustrated in FIG. 9B is input thereto.

For example, the learning function 352 adjusts the parameters of the neural network, so as to minimize the difference between the output of the neural network and the output-side data illustrated in FIG. 9B. As a result, the learning function 352 is able to generate the trained model M2 functioned to receive an input of a TDC and timing and to output the difference between the input timing and highly appropriate timing. Further, the learning function 352 stores the generated trained model M2 into the model memory 34.

Further, although the example was explained in which the trained model M2 is structured with the convolutional neural network, the trained model M2 may be structured with a recurrent neural network or may be generated by using a machine learning method other than neural networks. Further, a trained model M2 may be generated for each of the sets made up of a target site of a main scan and a target site of a pre-scan.

Figure 10:
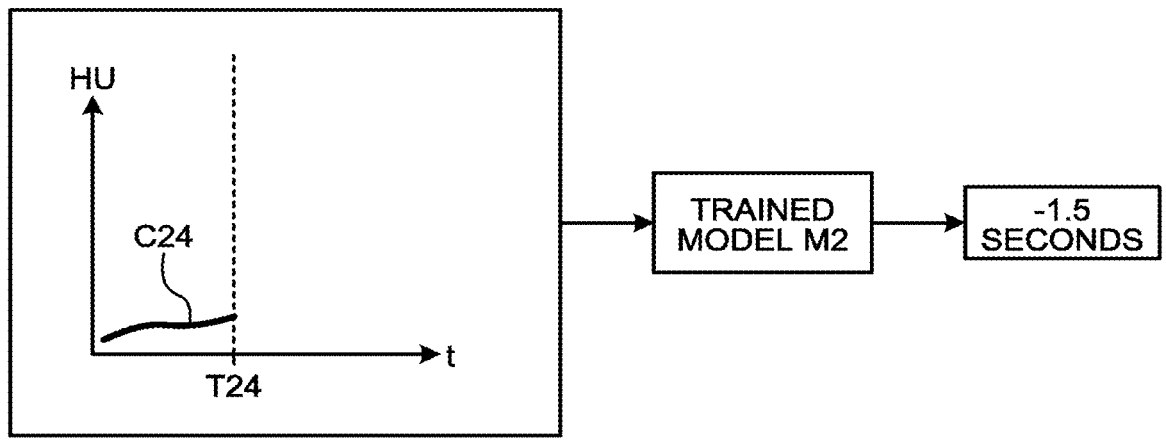
FIG. 10 is a drawing illustrating an example of use of the trained model according to the second embodiment.

After the trained model M2 has been generated and stored in the model memory 34, the determining function 353 determines appropriate timing of the transition from the pre-scan to the main scan in the second examination, by using the trained model M2. In the following sections, an example of use of the trained model M2 will be explained with reference to FIG. 10. FIG. 10 is a drawing illustrating the example of the use of the trained model M2 according to the second embodiment. With reference to FIG. 10, the example will be explained in which, in an examination E24 performed on a patient P24, appropriate timing of the transition from the pre-scan to the main scan is determined by using the trained model M2. The patient P24 is an example of the patient P illustrated in FIG. 2.

In the examination E24, at first, the system controlling function 144a sets a target site of the main scan and a target site of the pre-scan. In the following sections, an example will be explained in which the target site of the main scan in the examination E24 is the "heart", whereas the target site of the pre-scan in the examination E24 is the "aorta". Subsequently, the system controlling function 144a performs the pre-scan on the "aorta" of the patient P24 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs the pre-processing processes on the projection data output from the DAS 118. Further, the generating function 144c sequentially generates image data on the basis of the projection data on which the pre-processing processes have been performed. Further, the controlling function 144d sequentially transmits the generated image data to the medical information processing apparatus 30. Further, the acquiring function 351 sequentially acquires the transmitted image data. Also, the acquiring function 351 sets a region of interest of the patient P24.

Subsequently, the acquiring function 351 acquires a TDC on the basis of signal intensities in the region of interest within the group of time-series image data acquired in the pre-scan. For example, the acquiring function 351 acquires the TDC by plotting HU values in the region of interest in correspondence with a time axis, with respect to the pieces of image data in the group of time-series image data. Further, every time image data is newly acquired from the X-ray CT apparatus 10, the acquiring function 351 sequentially updates the TDC, by plotting the HU values in the region of interest in the newly-acquired image data in correspondence with the time axis. In the following sections, the TDC updated up to a time T24 in FIG. 10 will be referred to as a TDC C24.

In this situation, the determining function 353 inputs the acquired TDC to the trained model M2. For example, at the time T24, the determining function 353 inputs the TDC C24 illustrated in FIG. 10 to the trained model M2. In this situation, the trained model M2 receives the input of the TDC C24 and the time T24 and outputs the difference "−1.5 seconds" between the time T24 and the highly appropriate timing for the examination E24. The notation "−1.5 seconds" indicates that the time T24 is 1.5 seconds earlier than the highly appropriate timing for the examination E24. In other words, the notation "−1.5 seconds" indicates that the highly appropriate timing for the examination E24 is 1.5 seconds later than the time T24. In that situation, the determining function 353 determines the time that is 1.5 seconds later than the time T24 as appropriate timing of the transition from the pre-scan to the main scan. In the following sections, the time that is 1.5 seconds later than the time T24 may be referred to as a time T241.

The time T24 illustrated in FIG. 10 may be a preset time or may be determined during the examination E24. For example, the time T24 is a time when a predetermined period of time has elapsed since the contrast agent is injected in the patient P24. In another example, the trained model M2 may output the difference between the input timing and the highly appropriate timing, together with a degree of accuracy. In that situation, the determining function 353 sequentially inputs acquired TDCs to the trained model M2 and determines a time for which the degree of accuracy output from the trained model M2 exceeds a threshold value as the time T24.

Further, the controlling function 354 transmits the determined time T241 to the X-ray CT apparatus 10. Further, the X-ray CT apparatus 10 transitions from the pre-scan to the main scan at the time T241 and acquires CT image data 1241 (not illustrated). In other words, the X-ray CT apparatus 10 transitions from the pre-scan to the main scan at the time T241 determined by using the trained model M2 and acquires the CT image data 1241. As a result of the transition to the main scan, the pre-scan ends, and the updating of the TDC also ends.

In another example, the determining function 353 sequentially inputs the acquired TDC to the trained model M1. Further, the trained model M2 sequentially outputs differences between the input timing and the highly appropriate timing for the examination E24. After that, the determining function 353 determines the time for which the difference output from the trained model M2 is substantially equal to "0", as appropriate timing of the transition from the pre-scan to the main scan. In the following sections, the time for which the difference output from the trained model M2 is substantially equal to "0" in the examination E24 may be referred to as a time T242.

Further, the controlling function 354 transmits the determined time T242 to the X-ray CT apparatus 10. Further, the X-ray CT apparatus 10 transitions from the pre-scan to the main scan at the time T242 determined by using the trained model M2 and acquires CT image data 1242 (not illustrated). In other words, as being triggered by the difference output from the trained model M2 becoming substantially equal to "0", the X-ray CT apparatus 10 transitions from the pre-scan to the main scan and acquires the CT image data 1242. As a result of the transition to the main scan, the pre-scan ends, and the updating of the TDC also ends.

Further, the learning function 352 may generate a trained model M2 by using the learning data acquired in the examination E24. For example, the learning function 352 acquires information about appropriateness of the time T241, on the basis of an examination purpose of the examination E24 and the CT image data 1241 acquired in the examination E24. Further, the learning function 352 updates the trained model M2 by using a TDC updated up to the time T241 in the examination E24 and the time T241 of the transition from the pre-scan to the main scan in the examination E24 as the input-side learning data and using the information about appropriateness of the time T241 as the output-side learning data. Alternatively, the learning function 352 acquires the information about appropriateness of the time T242 on the basis of an examination purpose of the examination E24 and the CT image data 1242 acquired in the examination E24. Further, the learning function 352 updates the trained model M2 by using a TDC updated up to the time T242 in the examination E24 and the time T242 of the transition from the pre-scan to the main scan in the examination E24 as the input-side learning data and using the information about appropriateness of the time T242 as the output-side learning data. In other words, after using the trained model M2 with respect to the examination E24, the learning function 352 acquires the learning data from the examination E24. In that situation, the examination E24 corresponds to both the first examination and the second examination. Further, the learning function 352 may generate a plurality of pieces of learning data on the basis of the learning data acquired in the single examination E24.

As explained above, the X-ray diagnostic system 1 according to the second embodiment is configured to generate the trained model M2 used for determining the appropriate timing of the transition from the pre-scan to the main scan in the second examination, by using the TDC acquired by the acquiring function 351 and the timing information about the timing of the transition from the pre-scan to the main scan in the first examination as the input-side learning data and using the information about appropriateness of the timing of the transition from the pre-scan to the main scan as the output-side learning data. Further, the information about appropriateness of the timing of the transition from the pre-scan to the main scan includes the difference between the timing of the transition from the pre-scan to the main scan in the first examination and the highly appropriate timing. Consequently, the X-ray diagnostic system 1 according to the second embodiment is able to appropriately determine the timing of the main scan by using the trained model M2.

For example, the X-ray diagnostic system 1 is configured to generate the trained model M2 by performing the machine learning, while using the specific numerical value indicating the difference between the timing of the transition from the pre-scan to the main scan in the first examination and the highly appropriate timing for the first examination, as the learning data. As a result, the X-ray diagnostic system 1 makes it possible to determine the timing of the main scan more appropriately, by enhancing the level of precision of the trained model M2.

The example was explained in which the acquiring function 351 acquires the group of time-series image data from the X-ray CT apparatus 10, sets the region of interest, and acquires the TDC; however, possible embodiments are not limited to this example. For instance, the acquiring function 351 may acquire a TDC generated by the X-ray CT apparatus 10 from the X-ray CT apparatus 10. Further, for example, the acquiring function 351 may acquire a group of time-series partial image data from the X-ray CT apparatus 10 and acquire a TDC on the basis of the acquired group of time-series partial image data. Further, as the time-series information about the signal intensities in the region of interest, the acquiring function 351 may acquire data other than TDCs.

In the first and the second embodiments above, the examples were explained in which the time-series information about the signal intensities in the region of interest is used as the input-side learning data for generating the trained models. In contrast, in a third embodiment, an example will be explained in which a group of time-series partial image data is used as input-side learning data.

The X-ray diagnostic system 1 according to the third embodiment has the same configuration as that of the X-ray diagnostic system 1 illustrated in FIGS. 1 and 2, while parts of the processes performed by the learning function 352 and the determining function 353 are different. In the following sections, some of the constituent elements having the same configurations as those explained in the first and the second embodiments will be referred to by using the same reference characters as those in FIGS. 1 and 2, and the explanations thereof will be omitted.

In the following sections, an example in which learning data is acquired in an examination E31 performed on a patient P31 will be explained. The patient P31 is an example of the patient P illustrated in FIG. 2. In the examination E31, at first, the system controlling function 144a sets a target site of the main scan and a target site of the pre-scan. In the following sections, an example will be explained in which the target site of the main scan in the examination E31 is the "heart", whereas the target site of the pre-scan in the examination E31 is the "aorta". Subsequently, the system controlling function 144a performs the pre-scan on the "aorta" of the patient P31 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs the pre-processing processes on the projection data output from the DAS 118. Further, the generating function 144c sequentially generates image data on the basis of the projection data on which the pre-processing processes have been performed. Further, the controlling function 144d sequentially transmits the generated image data to the medical information processing apparatus 30. Also, the acquiring function 351 sequentially acquires the transmitted image data.

Further, the acquiring function 351 sets a region of interest of the patient P31. In other words, the acquiring function 351 acquires a group of time-series partial image data corresponding to the region of interest, by acquiring the group of time-series image data from the X-ray CT apparatus 10 and also setting the region of interest. Instead of the group of time-series image data, the acquiring function 351 may acquire a group of time-series partial image data from the X-ray CT apparatus 10.

Subsequently, the determining function 353 determines the timing of the transition from the pre-scan to the main scan in the examination E31. In the following sections, an example will be explained in which a time T31 is determined as the timing of the transition from the pre-scan to the main scan in the examination E31. The determining function 353 may determine the time T31 by using the threshold value A11, may determine the time T31 by using the trained model M1, may determine the time T31 by using the trained model M2, or may determine the time T31 by using a trained model M3 (explained later).

Subsequently, the learning function 352 acquires information about appropriateness of the time T31 of the transition from the pre-scan to the main scan in the examination E31. For example, the learning function 352 acquires the information about appropriateness of the time T31, on the basis of an examination purpose of the examination E31 and CT image data 131 acquired in the main scan in the examination E31. For example, as the information about appropriateness of the time T31, the learning function 352 acquires information indicating to which one of the classes among "appropriate", "early", and "later", the time T31 corresponds. Alternatively, as the information about appropriateness of the time T31, the learning function 352 may acquire the difference between the time T31 and highly appropriate timing for the examination E31.

After that, the learning function 352 generates the trained model M3 used for determining appropriate timing of the transition from the pre-scan to the main scan, by using the group of time-series partial image data and timing information about the timing of the transition from the pre-scan to the main scan as input-side learning data and using the information about appropriateness of the timing of the transition from the pre-scan to the main scan as output-side learning data. For example, the learning function 352 uses the group of partial image data acquired in the examination E31 and the time T31 of the transition from the pre-scan to the main scan in the examination E31 as the input-side learning data. Further, the learning function 352 uses the information about appropriateness of the time T31 as the output-side learning data.

For example, the learning function 352 generates the trained model M3 by performing deep learning on a multi-layer neural network. In one example, the learning function 352 inputs the group of partial image data acquired in the examination E31 and the time T31 to the neural network. In this situation, in the neural network, for example, information is propagated while only adjacent layers are linked together in one direction from the input-layer side toward the output-layer side.

For example, in a plurality of intermediate layers in the neural network, features are extracted through convolutions and pooling with respect to the region of interest, so as to perform a class categorization in all the linked layers. Further, results of the categorization into the three classes of "early", "appropriate", and "late" are output from the output layer of the neural network. Further, the learning function 352 adjusts parameters of the neural network so that the neural network is able to output desirable results when the input-side learning data is input thereto. For example, the learning function 352 adjusts the parameters of the neural network so as to eliminate inconsistency between outputs of the neural network and the output-side data. As a result, the learning function 352 is able to generate a trained model M31 functioned to receive an input of a group of partial image data and timing and to output information indicating to which one of the classes among "early", "appropriate", and "late", the input timing corresponds. Further, the learning function 352 stores the generated trained model M31 into the model memory 34. The trained model M31 is an example of the trained model M3.

Although the example of the trained model M31 structured with the convolutional neural network was explained, possible embodiments are not limited to this example. For instance, the trained model M3 may be structured with a recurrent neural network or may be generated by using a machine learning method other than neural networks. Further, a trained model M3 may be generated for each of the sets made up of a target site of a main scan and a target site of a pre-scan.

After the trained model M3 has been generated and stored in the model memory 34, the determining function 353 determines appropriate timing of the transition from the pre-scan to the main scan in the second examination by using the trained model M3. For example, in an examination E32 performed on a patient P32, the determining function 353 determines the appropriate timing of the transition from the pre-scan to the main scan, by using the trained model M3. The patient P32 is an example of the patient P illustrated in FIG. 2.

In the examination E32, at first, the system controlling function 144a sets a target site of the main scan and a target site of the pre-scan. In the following sections, an example will be explained in which the target site of the main scan in the examination E32 is the "heart", whereas the target site of the pre-scan in the examination E32 is the "aorta". Subsequently, the system controlling function 144a performs the pre-scan on the "aorta" of the patient P32 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs the pre-processing processes on the projection data output from the DAS 118. Further, the generating function 144c sequentially generates image data on the basis of the projection data on which the pre-processing processes have been performed. Further, the controlling function 144d sequentially transmits the generated image data to the medical information processing apparatus 30. Also, the acquiring function 351 sequentially acquires the transmitted image data.

Further, the acquiring function 351 sets a region of interest of the patient P32. In other words, the acquiring function 351 acquires a group of time-series partial image data corresponding to the region of interest, by acquiring the group of time-series image data from the X-ray CT apparatus 10 and also setting the region of interest. In this situation, every time the acquiring function 351 newly acquires image data from the X-ray CT apparatus 10, the group of time-series partial image data is updated.

Alternatively, instead of the group of time-series image data, the acquiring function 351 may acquire a group of time-series partial image data from the X-ray CT apparatus 10. In that situation, every time the acquiring function 351 newly acquires partial image data from the X-ray CT apparatus 10, the group of time-series partial image data acquired by the acquiring function 351 is updated.

Subsequently, the determining function 353 determines appropriate timing, which is a time T32, of the transition from the pre-scan to the main scan in the examination E32, by inputting the acquired group of time-series partial image data to the trained model M3. Further, the controlling function 354 transmits the determined time T32 to the X-ray CT apparatus 10. Further, the X-ray CT apparatus 10 transitions from the pre-scan to the main scan at the time T32 and acquires CT image data 132 (not illustrated). In other words, the X-ray CT apparatus 10 transitions from the pre-scan to the main scan at the time T32 determined by using the trained model M3 and acquires the CT image data 132. As a result of the transition to the main scan, the pre-scan ends, and the updating of the group of time-series partial image data also ends.

Further, the learning function 352 may generate a trained model M3 by using the learning data acquired in the examination E32. For example, the learning function 352 acquires information about appropriateness of the time T32, on the basis of an examination purpose of the examination E32 and the CT image data 132 acquired in the examination E32. Further, the learning function 352 updates the trained model M3, by using the group of time-series partial image data updated up to the time T32 in the examination E32 and the time T32 of the transition from the pre-scan to the main scan in the examination E32 as input-side learning data and using the information about appropriateness of the time T32 as output-side learning data. In other words, after using the trained model M3 with respect to the examination E32, the learning function 352 acquires the learning data from the examination E32. In that situation, the examination E32 corresponds to both the first examination and the second examination. Further, the learning function 352 may generate a plurality of pieces of learning data, on the basis of the learning data acquired in the single examination E32.

As explained above, in the third embodiment, the acquiring function 351 is configured to acquire the group of time-series partial image data being generated on the basis of the group of time-series image data acquired by performing the pre-scan on the patient injected with the contrast agent in the first examination using the X-ray diagnostic system 1 and corresponding to the region of interest of the patient. Further, the learning function 352 is configured to generate the trained model M3 used for determining the appropriate timing of the transition from the pre-scan to the main scan in the second examination, by using the group of time-series partial image data acquired by the acquiring function 351 and the timing information about the timing of the transition from the pre-scan to the main scan in the first examination as the input-side learning data and using the information about appropriateness of the timing of the transition from the pre-scan to the main scan in the first examination as the output-side learning data. Consequently, the X-ray diagnostic system 1 according to the third embodiment is able to appropriately determine the timing of the main scan by using the trained model M3, without acquiring the time-series information about the signal intensities in the region of interest of the patient P.

In the first to the third embodiments above, the examples were explained in which either the time-series information about the signal intensities in the region of interest or the group of time-series partial image data is used as the input-side learning data for generating the trained model. In contrast, in a fourth embodiment, an example will be explained in which a group of time-series image data is used as input-side learning data.

The X-ray diagnostic system 1 according to the fourth embodiment has the same configuration as that of the X-ray diagnostic system 1 illustrated in FIGS. 1 and 2, while parts of the processes performed by the learning function 352 and the determining function 353 are different. In the following sections, some of the constituent elements having the same configurations as those explained in the first and the second embodiments will be referred to by using the same reference characters as those in FIGS. 1 and 2, and the explanations thereof will be omitted.

In the following sections, an example will be explained in which learning data is acquired in an examination E41 performed on a patient P41. The patient P41 is an example of the patient P illustrated in FIG. 2. In the examination E41, at first, the system controlling function 144*a* sets a target site of the main scan and a target site of the pre-scan. In the following sections, an example will be explained in which the target site of the main scan in the examination E41 is the "heart", whereas the target site of the pre-scan in the examination E41 is the "aorta". Subsequently, the system controlling function 144*a* performs the pre-scan on the "aorta" of the patient P41 injected with a contrast agent. Further, while the pre-scan is performed by the system controlling function 144*a*, the DAS 118 acquires signals of the X-rays from the detecting elements included in the X-ray detector 112 and sequentially generates projection data. Further, the pre-processing function 144*b* sequentially performs the pre-processing processes on the projection data output from the DAS 118. Further, the generating function 144*c* sequentially generates image data on the basis of the projection data on which the pre-processing processes have been performed. Further, the controlling function 144*d* sequentially transmits the generated image data to the medical information processing apparatus 30. Also, the acquiring function 351 sequentially acquires the transmitted image data.

Subsequently, the determining function 353 determines the timing of the transition from the pre-scan to the main scan in the examination E41. In the following sections, an example will be explained in which a time T41 is determined as the timing of the transition from the pre-scan to the main scan in the examination E41. The determining function 353 may determine the time T41 by using the threshold value A11, may determine the time T41 by using the trained model M1, may determine the time T41 by using the trained model M2, may determine the time T41 by using the trained model M3, or may determine the time T41 by using a trained model M4 (explained later).

After that, the learning function 352 acquires information about appropriateness of the time T41 of the transition from the pre-scan to the main scan in the examination E41. For example, the learning function 352 acquires the information about appropriateness of the time T41, on the basis of an examination purpose of the examination E41 and CT image data 141 acquired in the main scan in the examination E41. For example, as the information about appropriateness of the time T41, the learning function 352 acquires information indicating to which one of the classes among "early", "appropriate", and "late", the time T41 corresponds. Alternatively, as the information about appropriateness of the time T41, the learning function 352 may acquire the difference between the time T41 and highly appropriate timing for the examination E41.

Subsequently, the learning function 352 generates the trained model M4 used for determining appropriate timing of the transition from the pre-scan to the main scan, by using the group of time-series image data and timing information about the timing of the transition from the pre-scan to the main scan as input-side learning data and using the information about appropriateness of the timing of the transition from the pre-scan to the main scan as output-side learning data. For example, the learning function 352 uses the group of image data acquired in the examination E41 and the time T41 of the transition from the pre-scan to the main scan in the examination E41 as the input-side learning data. Further, the learning function 352 uses the information about appropriateness of the time T41 as the output-side learning data.

For example, the learning function 352 generates the trained model M4 by performing deep learning on a multi-layer neural network. In one example, the learning function 352 inputs the group of image data acquired in the examination E41 and the time T41 to the neural network. In this situation, in the neural network, for example, information is propagated while only adjacent layers are linked together in one direction from the input-layer side toward the output-layer side.

For example, in a plurality of intermediate layers in the neural network, features are extracted through convolutions and pooling with respect to the image data, so as to perform a class categorization in all the linked layers. Further, results of the categorization into the three classes of "early", "appropriate", and "late" are output from the output layer of the neural network. Further, the learning function 352 adjusts parameters of the neural network so that the neural network is able to output desirable results when the input-side learning data is input thereto. For example, the learning function 352 adjusts the parameters of the neural network so as to eliminate inconsistency between outputs of the neural network and the output-side data. As a result, the learning function 352 is able to generate a trained model M41 functioned to receive an input of a group of image data and timing and to output information indicating to which one of the classes among "early", "appropriate", and "late", the input timing corresponds. Further, the learning function 352 stores the generated trained model M41 into the model memory 34. The trained model M41 is an example of the trained model M4.

Although the example of the trained model M41 structured with the convolutional neural network was explained, possible embodiments are not limited to this example. For instance, the trained model M4 may be structured with a recurrent neural network or may be generated by using a machine learning method other than neural networks. Further, a trained model M4 may be generated for each of the sets made up of a target site of a main scan and a target site of a pre-scan. Also, a trained model M4 may be structured by combining a trained model functioned to receive an input of a group of image data and to identify a region of interest, with the trained model M3.

After the trained model M4 has been generated and stored in the model memory 34, the determining function 353 determines appropriate timing of the transition from the pre-scan to the main scan in the second examination, by using the trained model M4. For example, in the examination E42 performed on a patient P42, the determining function 353 determines appropriate timing of the transition from the pre-scan to the main scan by using the trained model M4. The patient P42 is an example of the patient P illustrated in FIG. 2.

In the examination E42, at first, the system controlling function 144a sets a target site of the main scan and a target site of the pre-scan. In the following sections, an example will be explained in which the target site of the main scan in the examination E42 is the "heart", whereas the target site of the pre-scan in the examination E42 is the "aorta". Subsequently, the system controlling function 144a performs the pre-scan on the "aorta" of the patient P42 injected with a contrast agent. Further, while the pre-scan is performed by the system controlling function 144a, the DAS 118 acquires signals of the X-rays from the detecting elements included in the X-ray detector 112 and sequentially generates projection data. Further, the pre-processing function 144b sequentially performs the pre-processing processes on the projection data output from the DAS 118. Further, the generating function 144c sequentially generates image data on the basis of the projection data on which the pre-processing processes have been performed. Also, the controlling function 144d sequentially transmits the generated image data to the medical information processing apparatus 30.

Further, the acquiring function 351 sequentially acquires the transmitted image data. In other words, the acquiring function 351 acquires the group of time-series image data from the X-ray CT apparatus 10. In this situation, every time image data is newly acquired from the X-ray CT apparatus 10, the group of time-series image data acquired by the acquiring function 351 is updated.

Subsequently, the determining function 353 determines appropriate timing, which is a time T42, of the transition from the pre-scan to the main scan in the examination E42, by inputting the acquired group of time-series image data to the trained model M4. Further, the controlling function 354 transmits the determined time T42 to the X-ray CT apparatus 10. Further, the X-ray CT apparatus 10 transitions from the pre-scan to the main scan at the time T42 and acquires CT image data 142 (not illustrated). In other words, the X-ray CT apparatus 10 transitions from the pre-scan to the main scan at the time T42 determined by using the trained model M4 and acquires the CT image data 142. As a result of the transition to the main scan, the pre-scan ends, and the updating of the group of time-series partial image data also ends.

Further, the learning function 352 may generate a trained model M4 by using the learning data acquired in the examination E42. For example, the learning function 352 acquires information about appropriateness of the time T42, on the basis of an examination purpose of the examination E42 and the CT image data 142 acquired in the examination E42. Further, the learning function 352 updates the trained model M4, by using the group of time-series image data updated up to the time T42 in the examination E42 and the time T42 of the transition from the pre-scan to the main scan in the examination E42 as input-side learning data and using the information about appropriateness of the time T42 as output-side learning data. In other words, after using the trained model M4 with respect to the examination E42, the learning function 352 acquires the learning data from the examination E42. In that situation, the examination E42 corresponds to both the first examination and the second examination. Further, the learning function 352 may generate a plurality of pieces of learning data, on the basis of the learning data acquired in the single examination E42.

As explained above, in the fourth embodiment, the acquiring function 351 is configured to acquire the group of time-series image data acquired by performing the pre-scan on the patient injected with the contrast agent in the first examination using the X-ray diagnostic system 1. Further, the learning function 352 is configured to generate the trained model M4 used for determining the appropriate timing of the transition from the pre-scan to the main scan in the second examination, by using the group of time-series image data acquired by the acquiring function 351 and the timing information about the timing of the transition from the pre-scan to the main scan in the first examination as the input-side learning data and using the information about appropriateness of the timing of the transition from the pre-scan to the main scan in the first examination as the output-side learning data. Consequently, the X-ray diagnostic system 1 according to the fourth embodiment is able to appropriately determine the timing of the main scan by using the trained model M4.

In a fifth embodiment, an example will be explained in which the timing of the main scan is determined, by further taking into consideration the image taking method used by the X-ray CT apparatus 10. The X-ray diagnostic system 1 according to the fifth embodiment has the same configuration as that of the X-ray diagnostic system 1 illustrated in FIGS. 1 and 2, while parts of the processes performed by the learning function 352, the determining function 353, and the controlling function 354 are different. In the following sections, some of the constituent elements having the same configurations as those explained in the first embodiment will be referred to by using the same reference characters as those in FIGS. 1 and 2, and the explanations thereof will be omitted.

For example, the learning function 352 is configured to generate, with respect to each of different image taking methods, a trained model used for determining appropriate timing of the transition from the pre-scan to the main scan in the second examination. For example, the learning function 352 generates the trained model M1, the trained model M2, the trained model M3, or the trained model M4 for each of the different image taking methods. In this situation, the image taking methods denote methods of the CT scans performed by the X-ray CT apparatus 10, such as a helical scan, a volume scan, and the like, for example.

The helical scan is an image taking method by which, while the rotating part of the X-ray CT apparatus 10 is being rotated, either the tabletop 133 or the gantry 110 is moved in the Z-axis direction illustrated in FIG. 2. By performing a helical scan, it is possible to image a wide area exceeding the size of the X-ray detector 112 in the row direction. For helical scans, normally, the position of the target site in the Z-axis direction is different between a pre-scan and a main scan. In those situations, after the transition is made from the pre-scan to the main scan, CT image data is acquired after further moving either the tabletop 133 or the gantry 110 in the Z-axis direction. In other words, in helical scans, there is a time lag between the transition to the main scan and the acquirement of the CT image data.

The volume scan is an image taking method implemented by rotating the rotating part, without moving the tabletop 133 or the gantry 110 in the Z-axis direction. For volume scans, normally, the image taking position in the Z-axis direction is the same between a pre-scan and a main scan. Consequently, in volume scans, there is hardly any time lag between the transition to the main scan and the acquirement of the CT image data.

In other words, the time lag that may occur between the transition to a main scan and the acquirement of CT image data varies among image taking methods. For this reason, appropriate timing of the transition from a pre-scan to a main scan also varies among the image taking methods. Consequently, the learning function 352 makes it possible to determine the timing of the main scan more appropriately, by generating a trained model for each of the different image taking methods.

In the following sections, an example will be explained in which the trained model M1 is generated. For example, the learning function 352 acquires a plurality of TDCs acquired in the first examination and categorizes the plurality of acquired TDCs according to the image taking methods. Further, the learning function 352 generates a trained model M1 for each of the image taking methods, by using the categorized TDCs and timing information as input-side learning data. In other words, the learning function 352 enhances the level of precision of the trained model M1, by performing machine learning specialized for each image taking method as a result of grouping together the image taking methods related to the input-side learning data. In one example, the learning function 352 generates a trained model M11 used for determining appropriate timing of the transition to the main scan performed as a helical scan and a trained model M12 used for determining appropriate timing of the transition to the main scan performed as a volume scan.

In another example, the learning function 352 may correct the information about appropriateness of the timing, in accordance with image taking methods. In other words, even with the same timing, appropriateness may vary depending on whether the main scan is a helical scan or a volume scan. Accordingly, the learning function 352 corrects the information about appropriateness of the timing, while taking into consideration changes in the appropriateness that may be caused by image taking methods being different.

In the following sections, an example of an examination E51 performed on a patient P51 will be explained. The patient P51 is an example of the patient P illustrated in FIG. 2. The example will be explained on the assumption that the main scan in the examination E51 is performed as a helical scan.

In the examination E51, for example, the acquiring function 351 acquires a TDC by plotting HU values in a region of interest in correspondence with a time axis, on the basis of a group of time-series image data acquired by performing a pre-scan on the patient P51 injected with a contrast agent. Further, every time image data is newly acquired from the X-ray CT apparatus 10, the acquiring function 351 sequentially updates the TDC, by plotting the HU values in the region of interest in the newly-acquired image data in correspondence with the time axis. Further, by inputting the TDC to the trained model M11, the acquiring function 351 determines a time T51 as appropriate timing of the transition to the main scan in the examination E51.

Further, the controlling function 354 transmits the determined time T51 to the X-ray CT apparatus 10. Further, the X-ray CT apparatus 10 transitions from the pre-scan to the main scan at the time T51 and acquires CT image data 151 (not illustrated) by performing a helical scan. In that situation, there is a time lag between the time T51 and the acquirement of the CT image data 151, in accordance with the distance between the target site of the pre-scan and the target site of the main scan. Further, as a result of the transition to the main scan, the pre-scan ends, and the updating of the TDC also ends.

Subsequently, the learning function 352 acquires learning data from the examination E51. For example, the learning function 352 acquires information about appropriateness of the time T51 as the timing of the transition to the main scan performed as a helical scan, on the basis of an examination purpose of the examination E51 and the CT image data 151 acquired in the examination E51. In the following sections, the information about appropriateness of the timing of the transition to the main scan performed as a helical scan may be referred to as appropriateness information Ih. In other words, the learning function 352 acquires the appropriateness information Ih on the basis of the examination purpose of the examination E51 and the CT image data 151 acquired in the examination E51.

Further, by correcting the appropriateness information Ih according to the image taking method, the learning function 352 acquires information about appropriateness of the time T51 as the timing of the main scan performed as a volume scan. In the following sections, the information about appropriateness of the timing of the transition to the main scan performed as a volume scan may be referred to as appropriateness information Iv.

In other words, the learning function 352 acquires the appropriateness information Iv, by correcting the appropriateness information Ih according to the image taking method. For example, when the appropriateness information Ih indicates "appropriate", "early" is acquired as the appropriateness information Iv. After that, by using the learning data acquired in the examination E51, the learning function 352 generates the trained model M11 used for determining appropriate timing of the transition to the main scan performed as a helical scan and the trained model M12 used for determining appropriate timing of the transition to the main scan performed as a volume scan.

For example, the learning function 352 uses a TDC updated up to the time T51 in the examination E51 and the time T51 of the transition from the pre-scan to the main scan in the examination E51 as input-side learning data and uses the appropriateness information Ih of the time T51 as output-side learning data. In this manner, the learning function 352 generates the trained model M11 used for determining the appropriate timing of the transition to the main scan performed as a helical scan.

Further, the learning function 352 uses a TDC updated up to the time T51 in the examination E51 and the time T51 of the transition from the pre-scan to the main scan in the examination E51 as input-side learning data and uses the appropriateness information Iv of the time T51 as output-side learning data. In this manner, the learning function 352 generates the trained model M12 used for determining the appropriate timing of the transition to the main scan performed as a volume scan.

In other words, after using the trained model M1 with respect to the examination E51, the learning function 352 acquires, from the examination E24, the learning data used for generating the trained model M11 and the learning data used for generating the trained model M12. In this situation, the examination E51 corresponds to both the first examination and the second examination. Further, the learning function 352 may generate a plurality of pieces of learning data used for generating the trained model M11, on the basis of the learning data used for generating the trained model M11 and acquired in the single examination E24. Further, the learning function 352 may generate a plurality of pieces of learning data used for generating the trained model M12, on the basis of the learning data used for generating the trained model M12 and acquired in the single examination E24.

In another example, the determining function 353 corrects the timing determined as the timing of the transition from the pre-scan to the main scan, in accordance with the image taking method of the second examination. In the following sections, an example of an examination E52 performed on a patient P52 will be explained. The patient P52 is an example of the patient P illustrated in FIG. 2. Further, the example will be explained on the assumption that the main scan in the examination E52 is performed as a volume scan.

In the examination E52, for example, the acquiring function 351 acquires a TDC by plotting HU values in a region of interest in correspondence with a time axis, on the basis of a group of time-series image data acquired by performing a pre-scan on the patient P52 injected with a contrast agent. Further, every time image data is newly acquired from the X-ray CT apparatus 10, the acquiring function 351 sequentially updates the TDC, by plotting the HU values in the region of interest in the newly-acquired image data in correspondence with the time axis.

Figure 11:
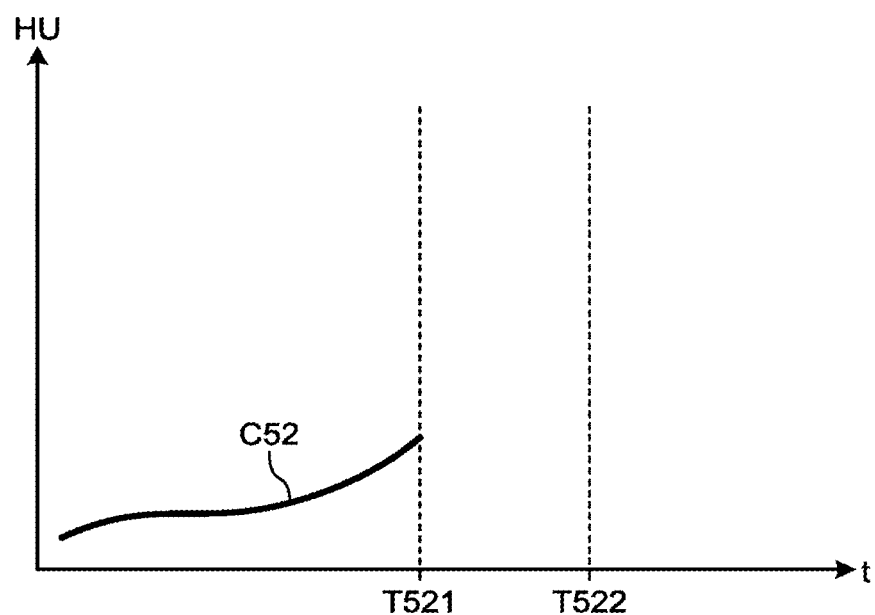
FIG. 11 is a drawing illustrating an example of timing of a transition from a pre-scan to a main scan according to a fifth embodiment.

Further, the determining function 353 determines a time T521 illustrated in FIG. 11, by inputting the TDC to the trained model M11. In the following sections, the TDC updated up to the time T521 will be referred to as a TDC C52. FIG. 11 is a drawing illustrating an example of the timing of the transition from the pre-scan to the main scan according to the fifth embodiment.

The time T521 illustrated in FIG. 11 is the timing determined as appropriate timing of the transition to the main scan performed as a helical scan. In this situation, because the main scan in the examination E52 is performed as a volume scan, the determining function 353 corrects the time T521 in accordance with the image taking method. For example, in volume scans, the time lag occurring between the transition to the main scan and the acquirement of the CT image data is shorter than the time lag occurring in helical scans. The timing of the transition to the main scan in a volume scan therefore can be later than that in a helical scan. Accordingly, as illustrated in FIG. 11, the determining function 353 delays the time T521 until a time T522.

Further, the controlling function 354 transmits the corrected time T522 to the X-ray CT apparatus 10. Further, the X-ray CT apparatus 10 transitions from the pre-scan to the main scan at the time T522 and acquires CT image data 152 (not illustrated) by performing the volume scan. In this situation, there is hardly any time lag between the time T52 and the acquirement of the CT image data 152. Further, as a result of the transition to the main scan, the pre-scan ends, and the updating of the TDC also ends. Further, the learning function 352 may acquire learning data from the examination E52.

As explained above, the X-ray diagnostic system 1 according to the fifth embodiment is configured to generate the trained model for each of the image taking methods. Consequently, the X-ray diagnostic system 1 according to the fifth embodiment is able to determine the timing of the main scan more appropriately, by generating the trained model that has learned the information including the differences that are caused depending on the image taking methods.

Further, as explained above, the X-ray diagnostic system 1 according to the fifth embodiment is configured to correct the timing determined as the timing of the transition from the pre-scan to the main scan, in accordance with the image taking method of the second examination. Consequently, the X-ray diagnostic system 1 according to the fifth embodiment is able to determine the timing of the main scan more appropriately, by correcting the differences that are caused depending on the image taking methods, without the need to generate a plurality of trained models.

The first to the fifth embodiments have thus been explained. It is, however, possible to carry out the present disclosure in various different forms other than those described in the first to the fifth embodiments.

For example, in the embodiments above, the example is explained in which the trained model is generated by using the group of time-series image data generated by the generating function 144c as the learning data; however, possible embodiments are not limited to this example. For instance, the learning function 352 may generate a trained model by processing the group of time-series image data generated by the generating function 144c and using the processed group of image data as learning data. In the following sections, the group of time-series image data generated by the generating function 144c may be referred to as a group of original image data.

In one example, the learning function 352 may generate a trained model, by using a group of image data generated by adding a body motion component to the group of original image data generated by the generating function 144c, as learning data. In this situation, the body motion component is, for example, a component caused by various types of body motion which the patient P has, such as heartbeats, respiration, swallowing, and the like.

For example, the learning function 352 generates the group of image data to which the body motion component is added, by translating or blurring the entire image with respect to a part or all of the image data included in the group of original image data, supposing that there was body motion during the acquisition of the group of original image data in the first examination. Further, the learning function 352 generates a trained model by using the group of image data to which the body motion component is added, as the learning data. Further, in the second examination, the determining function 353 determines appropriate timing of the transition from the pre-scan to the main scan in the second examination, by inputting input data including a group of time-series image data acquired in the pre-scan to the trained model.

In this situation, even when there is body motion during the pre-scan in the second examination, the X-ray diagnostic system 1 makes it possible to determine the timing of the main scan more appropriately while taking impacts of the body motion into consideration. In other words, when the timing of the main scan is determined on the basis of the signal intensities in a fixed region of interest in the pre-scan, there is a possibility that it may be impossible to appropriately determine the timing of the main scan, because of changes caused by the body motion in the positional relationship between the region of interest and the patient P. To cope with this situation, the X-ray diagnostic system 1 is able to appropriately determine the timing of the main scan, by continuing, when there is any body motion, to monitor the signal intensities in the region of interest by tracking the movements.

Further, the example was explained in which the group of image data generated by adding the body motion component to the group of time-series original image data is used as the learning data; however, it is also acceptable to generate a group of partial image data from the group of image data generated by adding the body motion component to the group of time-series original image data and to use the group of partial image data as learning data. Alternatively, it is also acceptable to generate a group of time-series partial image data from the group of time-series original image data and to use a group of partial image data generated by adding the body motion component to the group of time-series partial image data as learning data. Further, it is also acceptable to use time-series information generated on the basis of the group of image data generated by adding the body motion component to the group of time-series original image data as learning data. Alternatively, it is also acceptable to generate time-series information from the group of time-series original image data and to use time-series information generated by adding the body motion component to the time-series information as learning data.

In another example, the learning function 352 may generate a trained model, by using a group of image data generated by adding artifacts to the group of original image data generated by the generating function 144c, as learning data. In this situation, types of the artifacts are not particularly limited. The artifacts may be: artifacts caused by hardware such as the X-ray tube 111, the X-ray detector 112, or the like; artifacts caused by image taking conditions; artifacts caused by the imaged subject (e.g., metal artifacts); artifacts caused by the reconstruction method, and/or the like.

In one example, to acquire a group of time-series image data, a technique is known by which a reconstruction is performed at a higher frame rate, instead of performing a reconstruction every time the projection data corresponding to 360 degrees is acquired. For example, the generating function 144c reconstructs first image data by using the projection data corresponding to 360 degrees. Subsequently, at the point in time when projection data corresponding to 60 degrees has newly been acquired, the generating function 144c replaces a part of the previously-used projection data corresponding to 360 degrees with the newly-acquired projection data corresponding to 60 degrees and further reconstructs second image data by using the projection data corresponding to 360 degrees resulting from the replacement. In that situation, the generating function 144c is able to reconstruct six pieces of image data every time projection data corresponding to 360 degrees is acquired. In other words, each piece of newly-acquired projection data corresponding to 60 degrees is used for the reconstruction of six pieces of image data. In this situation, when any piece of newly-acquired projection data corresponding to 60 degrees has a defect, this defect affects each of the six pieces of image data. For example, when a newly-acquired piece of projection data corresponding to 60 degrees has a defect, a linear shadow corresponding to the X-ray tube position appears in each of the six pieces of image data. When these pieces of image data are continuously displayed, the defect may appear as a radar-like artifact. The learning function 352 may generate a trained model by using a group of image data generated by adding such a radar-like artifact to the group of original image data generated by the generating function 144c, as learning data.

For example, the learning function 352 acquires an artifact image exhibiting artifacts. In this situation, it is possible to generate the artifact image by performing a difference calculating process between image data containing the artifacts and image data containing no artifacts. The image data containing the artifacts and the image data containing no artifacts may be acquired by using a phantom simulating a human body as an imaged subject. Further, it is possible to generate an artifact image for each of different types of artifacts.

Further, the learning function 352 adds the artifacts to the group of original image data by combining the group of original image data generated by the generating function 144c with the artifact image. Further, the learning function 352 generates the trained model by using the group of image data to which the body motion component is added, as learning data. Further, in the second examination, the determining function 353 determines appropriate timing of the transition from the pre-scan to the main scan in the second examination, by inputting input data including a group of time-series image data acquired in the pre-scan to the trained model. In that situation, even when the group of original image data from the second examination contains artifacts, the X-ray diagnostic system 1 is able to appropriately determine the timing of the main scan while taking impacts of the artifacts into consideration.

In another example, the learning function 352 may generate a trained model, by using a group of image data generated by reducing artifacts from the group of original image data generated by the generating function 144c in the first examination, as learning data. Further, in the second examination, the determining function 353 determines appropriate timing of the transition from the pre-scan to the main scan in the second examination, by performing an artifact reducing process on the group of time-series image data acquired in the pre-scan and inputting input data including the artifact-reduced group of image data to the trained model. In that situation, the X-ray diagnostic system 1 is able to appropriately determine the timing of the main scan, by lowering impacts of the artifacts, at the times of generating and of using the trained model.

Further, the examples have so far been explained in which the group of image data generated by appending the artifacts to the group of time-series original image data or by reducing the artifacts from the group of time-series original image data is used as the learning data; however, possible embodiments are not limited to these examples. For instance, it is also acceptable to generate a group of partial image data from the group of image data generated by appending the artifacts to the group of time-series original image data or by reducing the artifacts from the group of time-series original image data and to further use the group of partial image data as learning data. Alternatively, it is also acceptable to generate a group of time-series partial image data from the group of time-series original image data and to further use a group of partial image data generated by appending artifacts to the group of time-series partial image data or reducing artifacts from the group of time-series partial image data, as learning data.

Further, it is also acceptable to use time-series information generated on the basis of the group of image data generated by appending artifacts to the group of time-series original image data or reducing artifacts from the group of time-series original image data, as learning data. Alternatively, it is also acceptable to generate time-series information from the group of time-series original image data and to further use time-series information generated by appending artifacts to the time-series information or reducing artifacts from the time-series information, as learning data. For example, when a TDC is used as the time-series information, the learning function 352 appends the radar-like artifact described above to the time-series information, by performing processing so that the TDC fluctuates along with the rotation cycle of the X-ray tube 111.

Further, the trained models explained in the above embodiments are examples and may be modified as appropriate. For example, the above embodiments describe the trained model M3 generated by using the group of time-series partial image data and the timing information about the timing of the transition from the pre-scan to the main scan as the input-side learning data and using the information about appropriateness of the timing of the transition from the pre-scan to the main scan as the output-side learning data. Further, the above embodiments describe the trained model M4 generated by using the group of time-series image data and the timing information about the timing of the transition from the pre-scan to the main scan as the input-side learning data and using the information about appropriateness of the timing of the transition from the pre-scan to the main scan as the output-side learning data. However, possible embodiments are not limited to these examples. For instance, it is also acceptable to generate a trained model by using a group of time-series partial image data and a group of time-series image data as well as the timing information about the timing of the transition from the pre-scan to the main scan as input-side learning data and using information about appropriateness of the timing of the transition from the pre-scan to the main scan as output-side learning data.

That is to say, it is possible to use any of the learning data explained in the above embodiments in combination, as appropriate. In other words, in the first examination, the acquiring function 351 is configured to acquire at least one selected from among: a group of time-series image data, a group of time-series partial image data, and time-series information in the region of interest. Further, the learning function 352 is configured to generate a trained model used for determining appropriate timing of the transition from the pre-scan to the main scan in the second examination, by using at least one selected from among the group of time-series image data acquired in the first examination, a group of time-series partial image data, and the time-series information in the region of interest as well as the timing information about the timing of the transition from the pre-scan to the main scan in the first examination as the input-side learning data and using the information about appropriateness of the timing of the transition from the pre-scan to the main scan in the first examination as the output-side learning data.

Further, in the embodiments above, the example was explained in which the timing information about the timing of the transition from the pre-scan to the main scan in the first examination is used as the input-side learning data; however, possible embodiments are not limited to this example. For instance, the learning function 352 may use values of the signal intensities in the region of interest of the patient, in place of the timing information.

For example, the learning function 352 is configured to generate the trained model M5, by using the TDC acquired in the first examination and the maximum value of the signal intensities indicated by the acquired TDC as input-side learning data and using the timing of the transition from the pre-scan to the main scan in the first examination as output-side learning data. In this situation, the maximum value of the signal intensities indicated by the TDC is normally the signal intensity in the region of interest in the piece of image data acquired most recently. For example, the trained model M5 is functioned to receive an input of the TDC and the maximum value of the signal intensities and to output information indicating to which one of the classes among "low", "appropriate", and "high", the input maximum value corresponds.

Subsequently, the acquiring function 351 is configured to acquire the TDC in the second examination, and the determining function 353 is configured to input the TDC to the trained model M5. In this situation, the trained model M5 is configured to output information indicating to which one of the classes among "low", "appropriate", and "high", the input maximum value of the signal intensities indicated by the TDC corresponds. In other words, by using a threshold value adjusted as appropriate by the trained model M5 as a reference, the trained model M5 outputs the information indicating which one of the classes among "low", "appropriate", and "high", the input maximum value of the signal intensities indicated by the TDC corresponds. Further, the determining function 353 determines the time indicated by the output from the trained model M5 as "appropriate", as the timing of the transition from the pre-scan to the main scan.

In the embodiments above, the example is explained in which the single appropriate time of the transition from the pre-scan to the main scan in the second examination is determined; however, possible embodiments are not limited to this example. For instance, when there are a plurality of targets sites of the main scan, the determining function 353 may determine appropriate timing of the transition from the pre-scan to the main scan, for each of the plurality of target sites.

Further, in the embodiments above, the example is explained in which the processing circuitry 35 included in the medical information processing apparatus 30 executes the acquiring function 351, the learning function 352, and the determining function 353; however, possible embodiments are not limited to this example. For instance, the processing circuitry 144 included in the X-ray CT apparatus 10 may execute functions corresponding to the acquiring function 351, the learning function 352, and the determining function 353.

Figure 12:
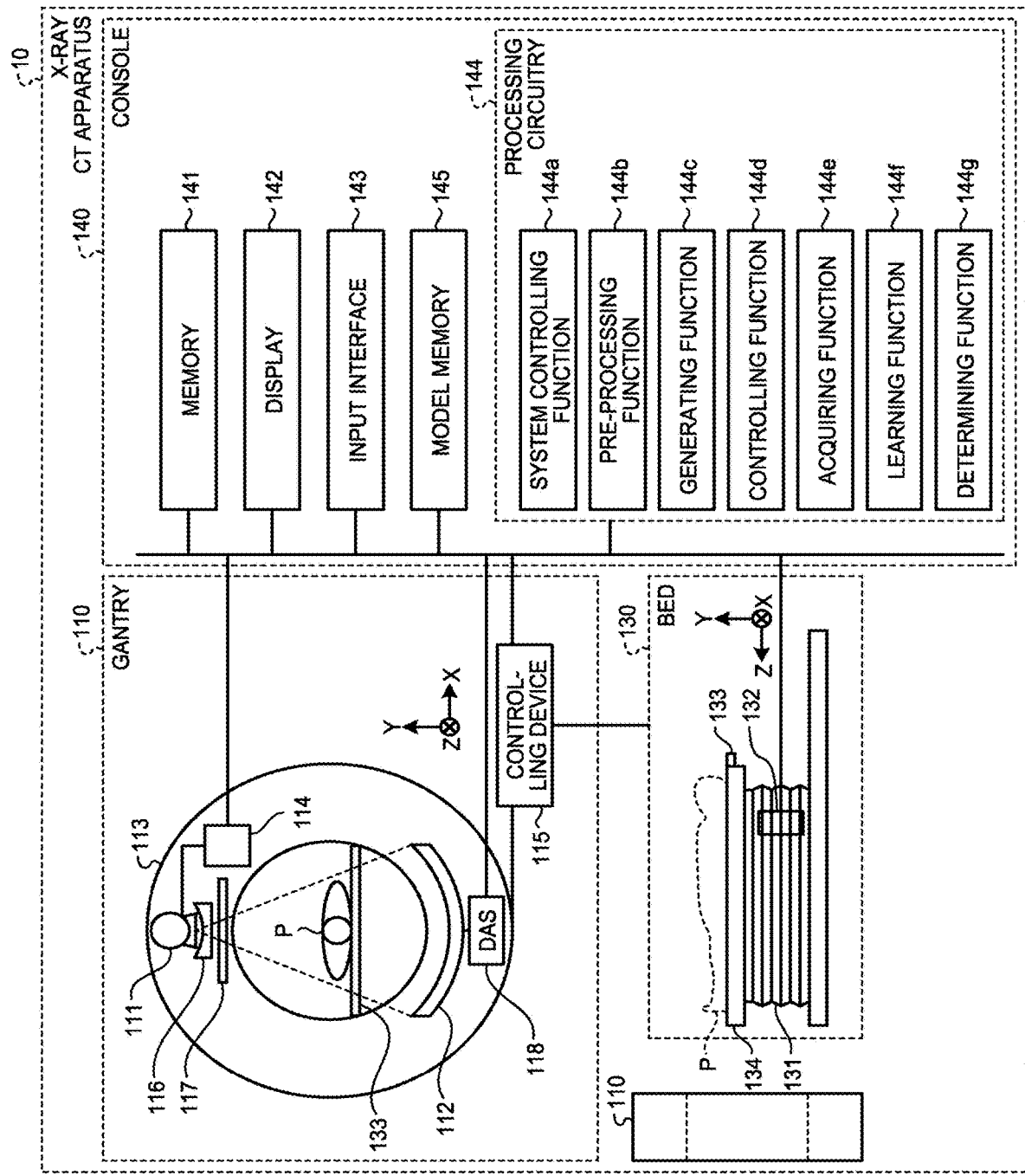
FIG. 12 is a block diagram illustrating an exemplary configuration of an X-ray CT apparatus according to a sixth embodiment.

For example, as illustrated in FIG. 12, in addition to the system controlling function 144a, the pre-processing function 144b, the generating function 144c, and the controlling function 144d, the processing circuitry 144 may further execute an acquiring function 144e, a learning function 144f, and a determining function 144g. The acquiring function 144e is a function corresponding to the acquiring function 351. The learning function 144f is a function corresponding to the learning function 352. The determining function 144g is a function corresponding to the determining function 353. Also, as illustrated in FIG. 12, the X-ray CT apparatus 10 further includes a model memory 145. FIG. 12 is a block diagram illustrating an exemplary configuration of the X-ray CT apparatus 10 according to a sixth embodiment.

In one example, in the first examination, the system controlling function 144a is configured to acquire a group of time-series image data by performing a pre-scan on a patient injected with a contrast agent. Further, the acquiring function 144e is configured to acquire at least one selected from among: a group of time-series image data, a group of time-series partial image data, and time-series information in a region of interest. Further, the learning function 352 is configured to generate a trained model used for determining appropriate timing of the transition from the pre-scan to the main scan in the second examination, by using at least one selected from among the group of time-series image data acquired in the first examination, the group of time-series partial image data, and the time-series information in the region of interest, as well as timing information about the timing of the transition from the pre-scan to the main scan in the first examination, as input-side learning data and using information about appropriateness of the timing of the transition from the pre-scan to the main scan in the first examination as output-side learning data. Further, the learning function 352 is configured to store the generated trained model into the model memory 145.

Further, in the second examination, the system controlling function 144a is configured to acquire a group of time-series image data, by performing a pre-scan on a patient injected with a contrast agent. Further, the acquiring function 144e is configured to acquire at least one selected from among: a group of time-series image data, a group of time-series partial image data, and time-series information in a region of interest. Further, the determining function 144g is configured to determine appropriate timing of the transition from the pre-scan to the main scan in the second examination, by acquiring at least one selected from among the group of time-series image data, the group of time-series partial image data, and the time-series information in the region of interest and inputting the acquired data and/or information to the trained model. Further, the system controlling function 144a is configured to transition from the pre-scan to the main scan with the timing determined by the determining function 144g and to acquire CT image data.

Further, in the embodiments above, the examples are explained in which either the learning function 352 or the learning function 144f generates the trained model. In other words, the above embodiments describe the examples in which one of the apparatuses included in the X-ray diagnostic system 1 generates the trained model; however, possible embodiments are not limited to these examples. The trained model may be generated by an external apparatus other than the apparatuses included in the X-ray diagnostic system 1. For example, the X-ray diagnostic system 1 is connected to the external apparatus via the network NW. Further, the external apparatus is configured to generate a trained model such as the trained model M1, M2, M3, M4, or M5 and to transmit the generated trained model to any of the apparatuses included in the X-ray diagnostic system 1. For example, the external apparatus transmits the generated trained model to the X-ray CT apparatus 10. In that situation, the acquiring function 144e is configured to acquire the trained models generated by the external apparatus and to store the acquired trained model into the model memory 145.

Further, in the embodiments above, the X-ray diagnostic system 1 was explained as an example of the medical image diagnostic system; however, possible embodiments are not limited to this example. For instance, the present disclosure is similarly applicable to a Magnetic Resonance Imaging (MRI) diagnostic system including an MRI apparatus, in place of the X-ray CT apparatus 10.

For example, when a main scan is performed by the MRI apparatus, a group of time-series image data is acquired by performing a pre-scan on a patient injected with a contrast agent. Further, the timing of the main scan is determined on the basis of the group of time-series image data, and the patient is instructed to hold his/her breath. Further, the main scan is performed on the patient P while he/she is holding his/her breath. In this situation, similarly to the situations with the X-ray CT apparatus 10, it is possible to appropriately determine the timing of the main scan performed by the MRI apparatus, by using any of the various types of trained models described above.

The pre-scan and the main scan in the embodiments described above are expressions simply indicating the temporal relationship between an earlier scan and a later scan. The expressions therefore do not indicate a superordinate-subordinate relationship between the scans.

The constituent elements of the apparatuses and the devices described in the above embodiments are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

Further, it is possible to realize the methods for generating the trained models and the methods for determining the timing of the transition to the main scan described in any of the above embodiments, by causing a computer such as a personal computer or a workstation to execute a program prepared in advance. It is possible to distribute the program via a network such as the Internet. Further, it is also possible to record the program onto a computer-readable recording medium such as a hard disk, a flexible disk (FD), a Compact Disk Read-Only Memory (CD-ROM), a Magneto Optical (MO) disk, a Digital Versatile Disk (DVD), or the like, so that the program is executed as being read from the recording medium by a computer.

According to at least one aspect of the embodiments described above, it is possible to appropriately determine the timing of the main scan.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnostic system comprising processing circuitry configured to: acquire a trained model generated by using, as learning data, (a) first time-series information indicating signal intensities in a first region of interest of a first patient generated on a basis of a first group of time-series images acquired by performing a first pre-scan on the first patient injected with a contrast agent in a first examination using the medical image diagnostic system, (b) timing information indicating timing of a transition from the first pre-scan to a first main scan in the first examination, and (c) information, based on image data obtained during the first main scan as opposed to the first pre-scan, indicating appropriateness of the timing; and determine, in a second examination different from the first examination, appropriate timing of a transition from a second pre-scan to a second main scan by inputting, to the trained model, second time-series information indicating signal intensities in a second region of interest of a second patient generated on a basis of a second group of time-series images acquired by performing a second pre-scan on the second patient injected with a contrast agent in the second examination different from the first examination.

2. The medical image diagnostic system according to claim 1, wherein the first group of time-series images is generated by adding a body motion component to a group of time-series original images.

3. The medical image diagnostic system according to claim 1, wherein the first time-series information includes information indicating a specific signal value band.

4. The medical image diagnostic system according to claim 1, wherein the first group of time-series images is generated by appending an artifact to a group of time-series original images or reducing an artifact from the group of time-series original images.

5. The medical image diagnostic system according to claim 1, wherein the trained model is generated by using an artifact image exhibiting an artifact appearing in the first time-series images, as learning data.

6. The medical image diagnostic system according to claim 1, wherein the information indicating appropriateness includes a difference between the timing of the transition from the first pre-scan to the first main scan and highly appropriate timing.

7. The medical image diagnostic system according to claim 1, wherein the information indicating appropriateness is information indicating to which one of options the timing of the transition from the first pre-scan to the first main scan corresponds, the options namely being highly appropriate timing, timing earlier than the highly appropriate timing, and timing later than the highly appropriate timing.

8. The medical image diagnostic system according to claim 7, wherein, on a basis of a set made up of information indicating that the timing of the transition from the first pre-scan to the first main scan corresponds to the timing later than the highly appropriate timing, and the first time-series information, as well as the timing information, at least one image selected from between the following is generated: (i) a set made up of information indicating that the timing of the transition from the first pre-scan to the first main scan corresponds to the highly appropriate timing, and the first time-series information having been processed, as well as the timing information having been processed; and (ii) a set made up of information indicating that the timing of the transition from the first pre-scan to the first main scan corresponds to the timing earlier than the highly appropriate timing, and the first time-series information having been processed, as well as the timing information having been processed, and the trained model is generated by further using the generated set as the learning data.

9. The medical image diagnostic system according to claim 6, wherein the information indicating appropriateness is acquired on a basis of an examination purpose of the first examination and one or more of the images acquired in the first examination.

10. The medical image diagnostic system according to claim 1, wherein the trained model is generated for each of plural groups of time-series images that are each made up of a target site of a pre-scan and a target site of a main scan.

11. The medical image diagnostic system according to claim 1, wherein the trained model is generated for each of plural image taking methods.

12. The medical image diagnostic system according to claim 11 wherein the trained model is generated for each of the plural image taking methods, by using, as the learning data, (e3) the first time-series information categorized in correspondence with the plural image taking methods.

13. The medical image diagnostic system according to claim 12, wherein the trained model is generated for each of the plural image taking methods, by correcting the information indicating the appropriateness of the timing in accordance with the plural image taking methods and using the corrected information as the learning data.

14. The medical image diagnostic system according to claim 1, wherein the timing information is a time at which any of the signal intensities in a region of interest of a patient within the images acquired in the first pre-scan exceeds a threshold value.

15. The medical image diagnostic system according to claim 1, wherein the timing information is a time when a predetermined period of time has elapsed since a time at which any of the signal intensities in a region of interest of a patient within the images acquired in the pre-scan of the first examination exceeded a threshold value.

16. The medical image diagnostic system according to claim 1, wherein the processing circuitry determines a plurality of appropriate times of transitions from the second pre-scan to a plurality of second main scans in the second examination.

17. The medical image diagnostic system according to claim 1, wherein the processing circuitry further corrects the determined timing in accordance with an image taking method used in the second examination.

18. A trained model generating method comprising: acquiring (a) first time-series information indicating signal intensities in a first region of interest of a first patient generated on a bask of a first group of time-series images acquired by performing a first pre-scan on the first patient injected with a contrast agent in a first examination using the medical image diagnostic system; and generating a trained model used for determining appropriate timing of a transition from a second pre-scan to a second main scan in a second examination different from the first examination, by using, as learning data, (a) the first time-series information, (b) timing information indicating timing of a transition from the first pre-scan to a first main scan in the first examination, and (c) information, based on image data obtained during the first main scan as opposed to the first pre-scan, indicating appropriateness of the timing.

19. A trained model generating method comprising: acquiring a trained model generated by using, as learning data, (a) first time-series information indicating signal intensities in a first region of interest of a first patient generated on a bask of a first group of time-series images acquired by performing a first pre-scan on the first patient injected with a contrast agent in a first examination using a medical image diagnostic system, (b) timing information indicating timing of a transition from the first pre-scan to a first main scan in the first examination, and (c) information, based on image data obtained during the first main scan as opposed to the first pre-scan, indicating appropriateness of the timing; and determining, in a second examination different from the first examination, appropriate timing of a transition from a second pre-scan to a second main scan by inputting, to the trained model, second time-series information indicating signal intensities in a second region of interest of a second patient generated on a basis of a second group of time-series images acquired by performing a second pre-scan on the second patient injected with a contrast agent in the second examination different from the first examination.

* * * * *